US007582472B2

(12) United States Patent
Smith et al.

(10) Patent No.: US 7,582,472 B2
(45) Date of Patent: Sep. 1, 2009

(54) APPARATUS AND METHOD FOR LIQUID SAMPLE TESTING

(76) Inventors: Kenneth E. Smith, P.O. Box 1292, Saco, ME (US) 04103; Haoyi Gu, 22 Waverly St., Portland, ME (US) 04072; Scott William Wagner, 44 Fieldstone Estates Rd., York, ME (US) 03909; Scott Marshall Clark, 6 Brentwood Rd., Cape Elizabeth, ME (US) 04107; Chun-Ming Chen, 17 Slocum Dr., Falmouth, ME (US) 04105

( * ) Notice: Subject to any disclaimer, the term of this patent is extended or adjusted under 35 U.S.C. 154(b) by 669 days.

(21) Appl. No.: 10/899,217

(22) Filed: Jul. 26, 2004

(65) Prior Publication Data

US 2005/0048597 A1 Mar. 3, 2005

Related U.S. Application Data

(60) Provisional application No. 60/497,767, filed on Aug. 26, 2003.

(51) Int. Cl.
*C12M 1/34* (2006.01)
*C12M 3/00* (2006.01)

(52) U.S. Cl. ........................ 435/288.4; 435/30; 435/40; 435/288.5

(58) Field of Classification Search ................. 204/451; 141/311; 422/61, 58, 55; 435/288.4, 287.2, 435/30, 40, 288.5
See application file for complete search history.

(56) References Cited

U.S. PATENT DOCUMENTS 3,901,658 A 8/1975 Burtis et al.

(Continued)

FOREIGN PATENT DOCUMENTS

DE 198 10 499 A1 9/1999

(Continued)

OTHER PUBLICATIONS

Meathrel W. G., Hand H. M. and Su Li-Hung. The effect of hydrophilic adhesives on sample flow. Jul./Aug. 2001. IVD Technology, pp. 1-13.*

(Continued)

*Primary Examiner*—Walter D Griffin
*Assistant Examiner*—Shanta G Doe
(74) *Attorney, Agent, or Firm*—Carter, DeLuca, Farrell & Schmidt LLP

(57) ABSTRACT

There is provided a device for partitioning a liquefied sample into discrete volumes. The device includes a bottom member; a top member disposed adjacent the bottom member; and at least one channel member disposed between the top and bottom members. The at least one channel member is at least partially defined by the top and bottom members and has first and second end portions. The first end portion of the at least one channel has an opening to receive liquid and the second end portion of the at least one channel has a reaction compartment and a vent opening. Accordingly, when the liquefied sample is introduced to the first end portion, capillary action assists in causing the liquefied sample to travel from the first end portion to the second end portion and at least a portion of the liquefied sample is caused to remain in the reaction compartment.

24 Claims, 20 Drawing Sheets

U.S. PATENT DOCUMENTS

| | | | | | |
|---|---|---|---|---|---|
| 4,070,249 | A | | 1/1978 | Janin et al. | |
| 4,073,693 | A | | 2/1978 | Janin | |
| 4,076,592 | A | | 2/1978 | Bradley | |
| 4,129,483 | A | | 12/1978 | Bochner | |
| 4,154,793 | A | | 5/1979 | Guigan | |
| 4,226,531 | A | | 10/1980 | Tiffany et al. | |
| 4,237,234 | A | | 12/1980 | Meunier | |
| 4,239,853 | A | | 12/1980 | Bradley | |
| 4,244,916 | A | | 1/1981 | Guigan | |
| 4,258,135 | A | | 3/1981 | Meunier | |
| 4,385,115 | A | | 5/1983 | de Zabala et al. | |
| 4,456,581 | A | | 6/1984 | Edelmann et al. | |
| 4,690,801 | A | | 9/1987 | Anderson | |
| 4,938,927 | A | | 7/1990 | Kelton et al. | |
| 5,110,555 | A | | 5/1992 | Moore et al. | |
| 5,141,875 | A | | 8/1992 | Kelton et al. | |
| 5,149,505 | A | | 9/1992 | English et al. | |
| 5,182,082 | A | | 1/1993 | Monthony et al. | |
| 5,186,897 | A | | 2/1993 | Eason et al. | |
| 5,338,666 | A | | 8/1994 | Monthony et al. | |
| 5,429,804 | A | | 7/1995 | Sayles | |
| 5,496,520 | A | | 3/1996 | Kelton et al. | |
| 5,518,892 | A | | 5/1996 | Naqui et al. | |
| 5,658,790 | A | * | 8/1997 | Gautsch | 435/404 |
| 5,700,655 | A | | 12/1997 | Croteau et al. | |
| 5,716,798 | A | * | 2/1998 | Monthony et al. | 435/34 |
| 5,753,456 | A | | 5/1998 | Naqui et al. | |
| 5,792,654 | A | | 8/1998 | Bohannon et al. | |
| 5,800,785 | A | | 9/1998 | Bochner | |
| 5,922,288 | A | | 7/1999 | Herst | |
| 5,985,594 | A | | 11/1999 | Croteau et al. | |
| 6,013,513 | A | | 1/2000 | Reber et al. | |
| 6,113,855 | A | | 9/2000 | Buechler | |
| 6,117,630 | A | | 9/2000 | Reber et al. | |
| 6,228,660 | B1 | | 5/2001 | May et al. | |
| 6,284,113 | B1 | * | 9/2001 | Bjornson et al. | 204/453 |
| 6,287,797 | B1 | | 9/2001 | Croteau et al. | |
| 6,355,449 | B1 | | 3/2002 | Chen et al. | |
| 6,387,650 | B1 | | 5/2002 | Townsend et al. | |
| 6,399,394 | B1 | | 6/2002 | Dahm et al. | |
| 6,416,642 | B1 | * | 7/2002 | Alajoki et al. | 204/451 |
| 6,426,230 | B1 | | 7/2002 | Feistel | |
| 6,472,167 | B1 | | 10/2002 | Townsend et al. | |
| 6,555,389 | B1 | | 4/2003 | Ullman et al. | |
| 6,632,656 | B1 | * | 10/2003 | Thomas et al. | 435/288.5 |
| 6,743,399 | B1 | * | 6/2004 | Weigl et al. | 422/102 |
| 2002/0106786 | A1 | * | 8/2002 | Carvalho et al. | 435/287.3 |
| 2003/0138941 | A1 | * | 7/2003 | Gong et al. | 435/287.2 |
| 2004/0115831 | A1 | * | 6/2004 | Meathrel et al. | 436/514 |
| 2004/0265172 | A1 | * | 12/2004 | Pugia et al. | 422/58 |

FOREIGN PATENT DOCUMENTS

| | | | |
|---|---|---|---|
| DE | 198 52 835 A1 | | 5/2000 |
| GB | 2 341 924 | | 3/2000 |
| WO | WO 99/55827 | * | 11/1999 |

OTHER PUBLICATIONS

International Search Report, PCT/US2004/027659, Aug. 25, 2004.

* cited by examiner

APPARATUS AND METHOD FOR LIQUID SAMPLE TESTING

CROSS-REFERENCE TO RELATED APPLICATIONS

The present application claims the benefit of and priority to U.S. Provisional Application Ser. No. 60/497,767, filed on Aug. 26, 2003, the entire contents of which being incorporated herein by reference.

BACKGROUND

1. Technical Field

The present disclosure relates to methods for the quantification of biological material in a sample, and to devices for partitioning and holding the biological material during quantification.

2. Discussion of Related Art

The determination and enumeration of microbial concentration is an essential part of microbiological analyses in many industries, including water, food, cosmetic, and pharmaceutical industries. The classical methods of detection and quantification of biological material are performed using semi-solid nutrient agar medium (e.g. pour plate method, membrane filtration) or liquid nutrient medium (e.g. the most probable number method). If a pour plate method is being performed, the sample being tested for microbial contamination is first dispensed in a Petri-dish. Then 15 ml of the appropriate nutrient medium is poured over the sample. The Petri-dish is then left to solidify at room temperature for approximately 20 minutes and then incubated at a specific temperature for a specific time, and any resulting colonies are counted. Drawbacks for the pour plate method include bacterial colonies, which may be too small or overlapping each other for counting and particulate matter in the samples, which may also interfere with counting. For the membrane filtration method, the required volume of sample is filtered through a membrane of a very small pore size to non-specifically trap bacteria. The membrane is then placed on a prepared solid medium, which supports the growth of the target bacteria. The medium is then incubated at a specific temperature for a specific time, and any resulting colonies are counted. Drawbacks of membrane filtration include particulate matter other than bacteria in the sample (e.g., a waste water sample) may clog the membrane making it unusable and bacterial colonies may be too small or overlapping each other making it difficult to count.

Improved methods using solid-base nutrient medium to support microbial growth for microbial detection and quantification include READIGEL® (3M Microbiology Products, St. Paul, Minn.), which uses a special chemically treated Petri-dish. The sample is inoculated into a growth medium and poured into the plate. The sample/medium mixture is solidified 20 minutes after it comes into contact with the chemicals coated in the plates. Alternatively, PETRIFILM® (3M Microbiology Products, St. Paul, Minn.), which is an adhesive tape-like material having a coated media deposited thereon may also be used. This arrangement forms a thin layer of growth media that hydrolyzes and gels upon contact with liquid samples. A cover piece helps to disburse the sample inoculums and also acts as a cover for incubation. These methods offer improvement over the pour plate and membrane filtration methods in that these methods are easier to perform. However, these methods suffer the same limitations as those of pour plate and membrane filtration methods as described above.

The most probable number method (MPN) is well known and described, for example, in Recles et al., "Most Probable Number Techniques" published in "Compendium of Methods for the Microbiological Examination of Foods", 3rd ed. 1992, at pages 105-199, and in Greenberg et al., "Standard Methods For the Examination of Water and Wastewater" (8th ed. 1992).

Microbial quantification devices and methods using the MPN method are commercially available. Devices and Methods such as Quanti-Tray® and Quanti-Tray® 2000 (IDEXX Corporation, Westbrook, Me.) are used for microbial quantification for drinking water, surface water, and waste water samples. A detailed disclosure of these tests may be found in Naqui et al. U.S. Pat. Nos. 5,518,892; 5,620,895; and 5,753,456. To perform these tests the separate steps of adding the sample/reagent to the device and then sealing the device with a separate sealing apparatus are required before the incubation period. These methods and devices offer a significant improvement over the traditional multiple tube fermentation techniques in terms of their ease of use and also allow for accurate quantification of microorganisms in the sample. However, devices of this type may require an instrument to distribute the sample/medium mixture into each individual compartment and are more applicable for enumerating microbial populations in the microaerophilic condition.

Croteau et al. also describe a method and device for quantification of biological material in a sample using the MPN method in U.S. Pat. Nos. 5,700,655; 5,985,594; and 6,287,797. The device uses a flat horizontal incubation plate and the surface is divided into a plurality of recessed wells. The liquefied sample/medium mixture is poured onto the surface of the device and after gentle mixing the sample/medium mixture is distributed into the recessed wells and held in the well by surface tension. The plate is then incubated at a specific temperature for a specific time until the presence or absence of the biological material is determined. Pierson et al. in U.S. Pat. No. 6,190,878, entitled "Methods and Devices for the Determination of Analyte in a Solution", disclose devices using a flat horizontal surface, which is divided into a plurality of recessed wells. Others have one or more surfaces with reagent islands immobilized thereon. Each well or wells or reagent islands are sized and shaped, and formed of a suitable material to hold the aliquot within the well or reagent islands by surface tension. These devices offer improvement over the gel-based methods for microbial enumeration by providing the benefit of easy result interpretation and higher counting ranges. These methods and devices potentially may have some disadvantages. Sample inoculation may be hampered by air bubbles, which form in the wells during the inoculation of samples and requires a pipetting step.

SUMMARY

The present invention provides methods and devices for detecting and quantification of the presence and absence of biological materials, microorganisms, and analytes in a liquefied sample solution. The invention makes use of "capillary flow", wherein a liquefied sample can be partitioned into discrete compartments through capillary channels. The present invention overcomes deficiencies of the prior art by providing devices and methods, which significantly reduce the amount of hands-on time and do not require skilled laboratory personnel to perform or interpret the assay.

In one aspect, the invention features a method for the quantification of target microorganisms by providing a target-microbe free incubation device to partition an aqueous or liquefied biological sample into discrete compartments. The device generally comprises a sample landing area, at least one capillary channel, and at least one recessed compartment each having a venting mechanism to allow functional capillary flow to take place. Each capillary channel is adapted to transport liquefied sample from the sample-landing zone to the recessed compartment. Preferably, each channel is either made of a material or treated with material suitable to facilitate capillary flow and has a geometry that also facilitates capillary flow. Each compartment is designed to hold an aliquot of sample/medium mixture for the detection of the biological material.

The device may be used in combination with a specific microbiological medium for determining the presence or amount of a specific type of biological material in a test sample. The microbiological medium is used to facilitate growth and to indicate the presence of target microorganisms. Depending on the test being performed different media may be utilized to detect different target microorganisms. The choice of the testing medium will depend on the biological material to be detected. The testing medium preferably only detects the presence of the biological material sought to be quantified, and preferably does not detect the presence of other biological material likely to be in the sample. The medium also preferably causes some visible or otherwise sensible change, such as color change or fluorescence, if the biological material sought to be detected is present in the sample. Generally, no positive response is detected in the absence of the target microorganisms. For example, Townsend et al., U.S. Pat. Nos. 6,387,650 and 6,472,167, describes a medium for the detection of bacteria in food and water samples. Alternatively, the medium of Edberg (U.S. Pat. Nos. 4,925,789; 5,429,933; and 5,780,259) or other microbiological media that are not based on the Edberg Defined Substrate Technology® media may be used to determine and quantify the amount of total coliforms and *Escherichia coli* in the devices of this invention. Also, the medium of Chen et al., U.S. Pat. No. 5,620,865, may be used to detect enterococci in a sample using this invention.

In a preferred embodiment, the medium is deposited into the sample landing area. Upon inoculation of a liquefied sample, the medium is reconstituted and mixed with the sample to form a sample/medium mixture and is partitioned into the recessed or reaction compartment through the adapted capillary channels via capillary flow. The medium may also be deposited in the capillary channels and/or the recessed or reaction compartments. The sample is partitioned through the adapted capillary channels to be mixed with the medium to form a sample/medium mixture. The device is then incubated to allow the detection of target biological material. The recessed or reaction compartment or compartments may contain a plurality of media, and different compartments may contain different medium or different combinations of different media, so that numerous assays may be performed on a single device. In another embodiment, the sample may be mixed with the medium to form a liquefied sample/medium mixture before inoculating onto the sample landing area of the device and then partitioned into the recessed or reaction compartment through capillary flow.

In one preferred embodiment, the device is constructed of plastic material through injection molding techniques and alternatively it may be constructed through other means. In a preferred embodiment, the plastic material is polystyrene. A preferred embodiment of the device is circular in shape; however, any suitable geometric configuration can be used such as rectangular, oval, or other. The reaction compartment may be of uniform size with each compartment having the capacity to hold a predetermined volume of the liquid. The reaction compartments may be round, teardrop, or other shaped geometry. The capillary channel may be adapted by treating with a capillary flow enhancing treatment to enhance the capillarity of the liquid in the channel. In a particular embodiment, the capillary flow enhancing treatment is corona treatment or other surface treatment to enhance the capillarity of the channels.

According to one aspect of the present disclosure, a device for partitioning a liquefied sample into discrete volumes is provided. The device includes a bottom member; a top member disposed adjacent the bottom member; and at least one channel member disposed between the top and bottom members. The at least one channel member is at least partially defined by the top and bottom members and having first and second end portions. The first end portion has an opening to receive liquid and the second end portion has a reaction compartment and an associated vent opening. Accordingly, when the liquefied sample is introduced to the first end portion, capillary action assists in causing the liquefied sample to travel from the first end portion to the second end portion and at least a portion of the liquefied sample is caused to remain in the reaction compartment.

In an embodiment, the top and bottom members of the device may have a central region for receiving a liquefied sample, and a plurality of channel members extend radially outward from the central region. Accordingly, when a liquefied sample is disposed in the central region, the sample flows into each channel member and portions of the liquefied sample become disposed in each reaction compartment of each channel member.

Desirably, at least one channel member is treated in a manner to enhance capillary flow of a liquid. More desirably, only the channel members are treated in a manner to enhance capillary flow of a liquid.

It is envisioned that the top member and the bottom member are made from polymethylpentene, polystyrene, polyester, polyolefin, or PETG.

In one embodiment, a medium is desirably disposed in a portion of the device. More desirably, the medium is disposed in each reaction compartment. The medium may be disposed in each channel and/or in the central region.

In another embodiment, the invention features a device having its capillary channels and target reaction compartments constructed by stacking two or more layers of plastic films. At least one or more surfaces of these plastic films are hydrophilic to promote or facilitate capillary flow of the liquefied sample. The lamination of the plastic films is achieved by using a pressure sensitive adhesive, a heat activated adhesive, a pressure sensitive transfer adhesive or a heat sensitive transfer adhesive. The layers of plastic films and adhesives comprise a hydrophilic top layer, a hydrophobic frame having at least one capillary channel, and a plastic backing layer. Preferably, the plastic material of the hydrophilic top layer is selected from clear polystyrene, polyester (PE), polyolefin, Polymethylpentene (PMP), or PETG, or any other clear plastic material. The hydrophobic frame layer, which forms at least a portion of the capillary channels, is made from material selected from the group consisting of polystyrene, polyester, PETG, or other similar polymers. The plastic backing layer can be a hydrophilic or hydrophobic plastic layer. It is preferably made of polystyrene, polyester (PE), PETG, polyolefin, or other material.

The device generally includes a sample landing zone, at least one capillary channel and at least one reaction compartment located within the capillary channel and each having a venting mechanism to facilitate the capillary flow. The sample landing area may be hydrophilic or hydrophobic in nature. Preferably, it is hydrophobic in nature to repel the liquefied sample or liquefied sample/medium mixture into the capillary channels and further to prevent the liquid from flowing back. Each capillary channel is adapted to partition a liquid sample from the sample-landing zone to the reaction compartment. Each compartment is designed to hold an aliquot of sample/medium mixture for the detection of the biological material.

In an alternative embodiment, the device may further include an absorbent pad at the bottom to absorb excess liquid or liquefied sample/medium mixture. The absorbent material can be a polyester foam, polyether foam or cellulose acetate, cotton fiber or absorbent material of other nature. Alternatively, an absorbent pad of like material may also be placed in the device cover or on top of the top layer of plastic film to absorb excess liquid or liquefied sample/medium mixture and aid humidification.

In a further preferred embodiment, a housing container is provided to hold and house the layers of plastic films. In one preferred embodiment, the layers of plastic films are held tightly in place by at least two (2) ribs on the inner diameter of the container bottom. In another embodiment, the housing container, is made of snug-fit top and bottom halves, and is used to hold and house the layers of plastic films.

In yet another preferred embodiment, the device is constructed through an injection mold technique by having the distribution channels and recessed wells molded directly on the bottom half of the housing container. One layer of the plastic film is laminated on top of the distribution channels and recessed wells to form capillary channels and target reaction compartments. The plastic film may be hydrophilic to promote or facilitate capillary flow of the liquefied sample. The plastic film may be selected from a pressure sensitive adhesive film or a heat activated adhesive film. Alternatively, the capillary channel may be adapted to enhance the capillarity of the liquid in the channel. The channel may be treated with a capillary flow enhancing coating. In a particular embodiment, the capillary flow enhancing treatment is corona treatment or other surface treatment to enhance the capillarity of the channels. Preferably, the plastic material of the top layer is selected from clear polystyrene, polyester (PE), Polymethylpentene (PMP), polyolefin, or PETG, or any other clear plastic material. The hydrophobic frame layer molded directly on the bottom of the housing container is made from material selected from the group consisting of polystyrene, polyester, PETG, or other similar polymers.

In another aspect, this invention provides a method of detecting one or more target analyte(s) or microorganism(s) in a test sample including the steps of: 1) contacting the test sample with the medium capable of detecting the presence of target biological material in the sample landing area; 2) partitioning the sample/medium mixture in through at least one capillary channel via capillary flow into the discrete reaction compartment(s); 3) subjecting the test device to reaction parameters which allow the development of a sensible signal; and 4) determining the presence of and enumerating the amount of target analyte(s) or microorganism(s).

In another aspect, the invention provides a method of detecting one or more target analyte(s) or microorganism(s) in a test sample including the steps of: 1) providing a device, which comprises the structure of at least one sample landing area, at least one capillary channel, and at least one reaction compartment deposited with one or more media capable of detecting the presence of target biological material; 2) adding the test sample to the sample landing area of the device; 3) partitioning the test sample through the at least one capillary channel via capillary flow into at least one discrete reaction compartment(s); 4) subjecting the test device to reaction parameters which allow the development of a sensible signal; and 5) determining the presence of and enumerating the amount of target analyte(s) or microorganism(s).

In yet another aspect, the invention provides a method of detecting one or more target analyte(s) or microorganism(s) in a test sample, which includes the steps of: 1) selecting and mixing a test medium suitable for detecting the target analyte(s) or microorganisms with the test sample to create a test solution; 2) providing a device, which includes one or more sample landing area(s), at least one partitioning channel having a substantially capillary structure, and at least one reaction compartment, which is capable of holding a predetermined amount of test solution; 3) adding the test solution to the device for a time sufficient to partition the test sample into the reaction compartments; and 4) subjecting the device in reaction parameters which allow the detection of the presence of and the enumeration of target analyte(s) and microorganism(s). In another embodiment, the providing step may further include a determining means which includes a medium (or use reagent) which produces a sensible signal that signifies the presence of or the amount of target analyte(s) or microorganism(s). In another embodiment, the allowing step may include subjecting the device to reaction parameters sufficient to allow development of the reagent. Another step may be added to the method including observing the determining, or a step of determining the presence of or the amount of target analyte(s) or microorganism(s), or a step of determining the quantity of target analyte(s) or microorganism(s).

BRIEF DESCRIPTION OF THE DRAWINGS

The foregoing advantages and features of the presently disclosed apparatus and methods for liquid sample testing will become more readily apparent and may be understood by referring to the following detailed description of illustrative embodiments, taken in conjunction with the accompanying drawings, in which.

DETAILED DESCRIPTION OF PREFERRED EMBODIMENTS

Figure 1:
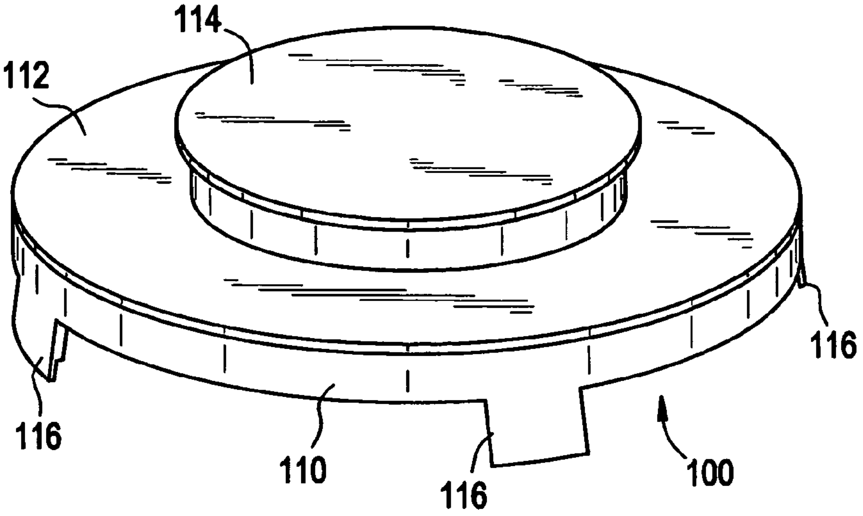
FIG. 1 is a perspective view of one illustrative embodiment of a liquid sample testing apparatus constructed in accordance with the present disclosure.

Referring now in specific detail to the drawings, in which like reference numerals identify similar or identical elements throughout the several views, the following detailed description will focus on specific exemplary embodiments of testing apparatus and methods. It is to be understood that the apparatus and methods disclosed herein may be adapted for use in testing for quantification of biological material as may be desired or necessary for a given application. Accordingly, the presently disclosed apparatus and methods are applicable to any biological material that it presents at any level in a liquefied sample (provided that one or more units of the material can be detected), and to any applicable testing medium. As used herein, a "liquefied sample" includes, but is not limited to, any sample that is a liquid or a sample that has been processed to act as a liquid.

Referring now to FIGS. 1-5, one illustrative embodiment of a testing apparatus specifically configured and adapted to achieve quantification based MPN methods is shown generally as disc assembly 100. In general, operation of the various test apparatus embodiments disclosed herein are based on capillary fluid dynamics to achieve an acceptable division and distribution of the liquefied sample into separate targeted compartments described in greater detail herein, without external forces from human manipulations. The end result is to yield visual binary signals for the quantitative detection of biological materials based on MPN.

Disc assembly 100 includes as its major structural components, a base 110, a lid 112 and a cap 114 which are assembled to form an integrated unit. Each of these components are preferably made from a durable material which provides sufficient structural strength such that a number of disc assemblies 100 may be stacked on top of each other as described in greater detail below. Examples of such material include but are not limited to acrylic, and polystyrene.

Figure 2:
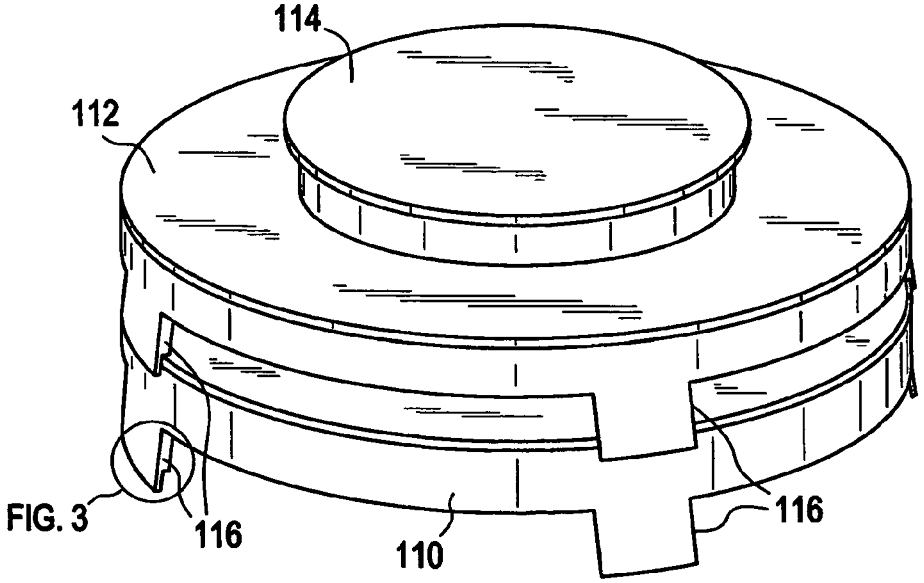
FIG. 2 is a perspective view of two of the testing apparatus of FIG. 1 shown in a stacked configuration.
Figure 3:
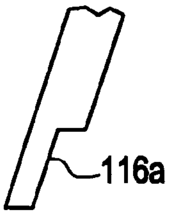
FIG. 3 is an enlarged partial view of a portion of a leg of the testing apparatus of FIG. 1.

Base 110 includes a series of legs 116 formed to extend downwardly from the bottom of the base and spaced around the periphery thereof. Each disc 100 is preferably provided with four legs 116 (only three legs 116 being seen in FIGS. 1 and 2). However, it is also contemplated that fewer or more than four legs may be utilized. Each of legs 116 may be flared outward to provide additional stability when resting disc 100 on a flat surface or on top of other discs 100. As an additional measure of stability, each leg 116 includes a notch or stepped end 116*a*, FIG. 3, to facilitate stacking of multiple discs 100 on top of each other as shown in FIG. 2. Stepped end 116*a* also prevents lateral movement of stacked discs relative to each other.

It is also contemplated that in environments where additional stability is desired or necessary, active retention of adjacently stacked members with respect to each other could also be provided by way of a retention mechanism. This may be useful, for example, in mobile applications or for tests performed where it is necessary or desirable to index the adjacent stacked discs 100 with respect to each other. In particular, where more than one media is utilized to perform multiple tests at the same time, disc assemblies 100 could be indexed to align the corresponding media of the wells of adjacently stacked disc assemblies 100. To facilitate indexing of adjacent stacked disc assemblies 100, indicia (not shown) can be provided on each disc assembly 100 to properly orient the discs relative to each other. Alternatively, the retention mechanism could be formed such that stacking of adjacent disc assemblies is only possible in one orientation of respectively stacked disc assemblies 100.

Figure 4:
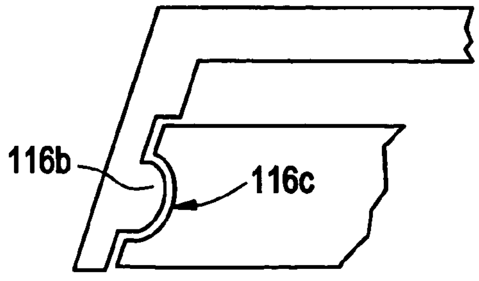
FIG. 4 is an enlarged partial view of an alternative leg configuration.

One example of a retention mechanism is shown in FIG. 4, wherein a detent mechanism is formed between the inner surface of stepped portion 116*a* and the corresponding outer surface of base 116 by having a protruding portion such as bump 116*b* formed on the inside surface of stepped portion 116*a* to be aligned with a complementary shaped depression such as a detent 116*c* formed on the outer surface of base 110. In this manner, when discs 100 are stacked on top of each other the detent mechanism would function to actively retain the adjacent discs from vertical or horizontal movement. Other types of retention mechanisms, for example, tabs and slots, hook and loop fasteners, snaps, friction fit complementary shaped surfaces, or the like, could also be used to maintain the relative positioning of a stacked series of discs 100.

Figure 5:
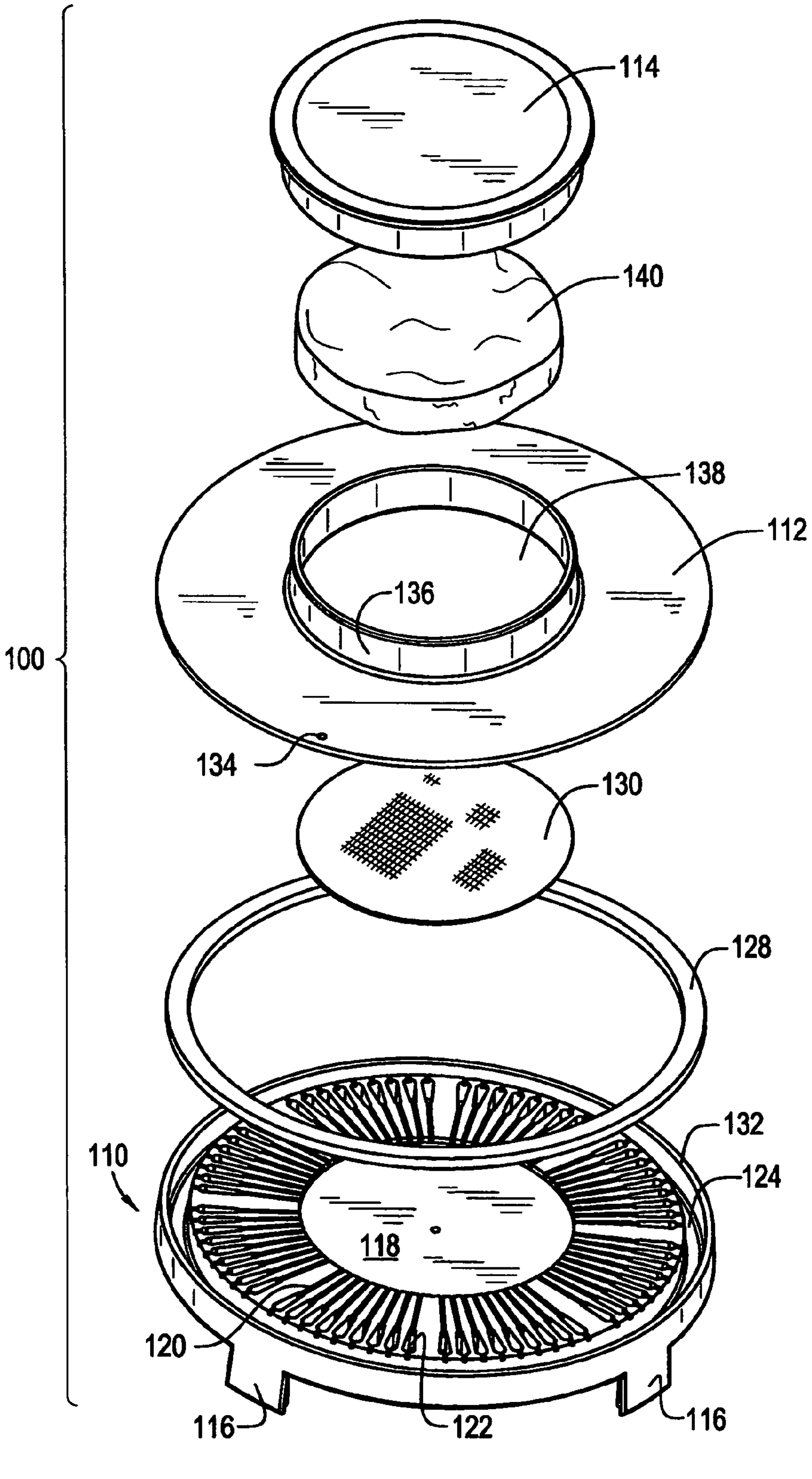
FIG. 5 is a perspective view with parts separated showing the various individual components of the testing apparatus of FIG. 1.
Figure 6:
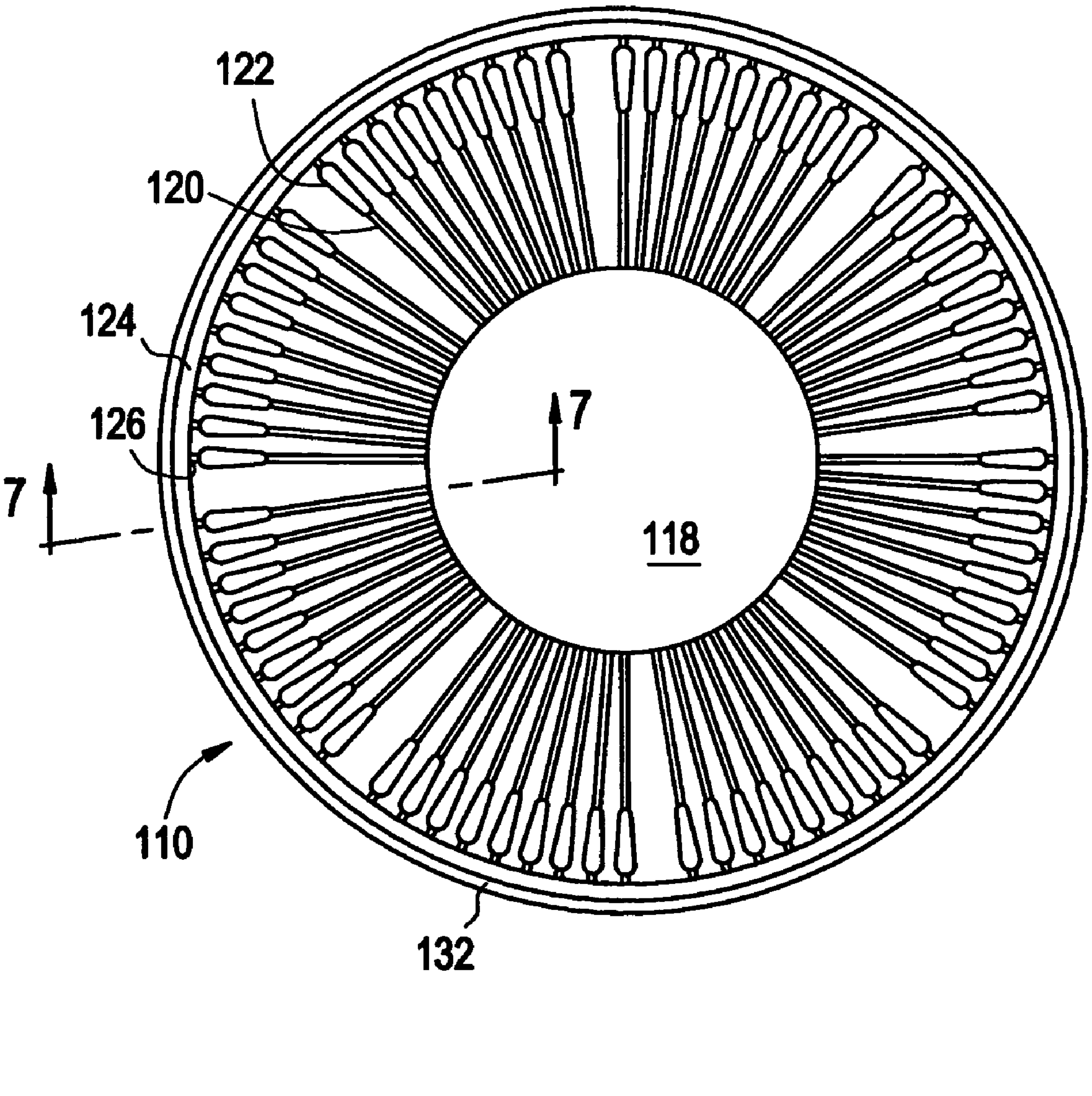
FIG. 6 is a top plan view of a multi-welled base of the testing apparatus of FIG. 1.
Figure 7:
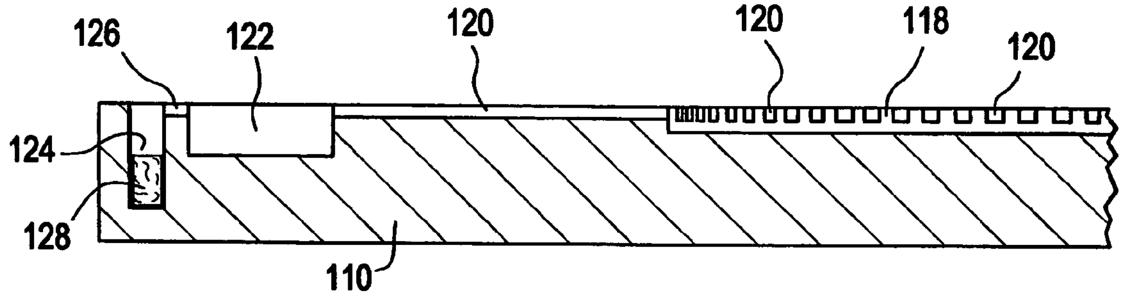
FIG. 7 is a partial cross-section view of the multi-welled base taken along section line 7-7 of FIG. 6.

Referring to FIGS. 5-8, base 110 further includes a central sample receiving well 118 and a plurality of individual radially arranged capillary channels 120 formed on the upper surface. Each of capillary channels 120 is in fluid communication at a first end with central well 118 at a uniform height above the bottom of central well 118 as best shown in FIG. 7. In this manner, a fluid sample poured into central well 118 first spreads evenly across the entire well surface and must rise to the level of the capillary channels 120 along the perimeter wall of central well 118. Thus, fluid will be distributed evenly to enter each of the capillary channels 120 substantially simultaneously. A plurality of target wells 122 are formed one each in fluid communication with respective capillary channels 120.

Figure 8:
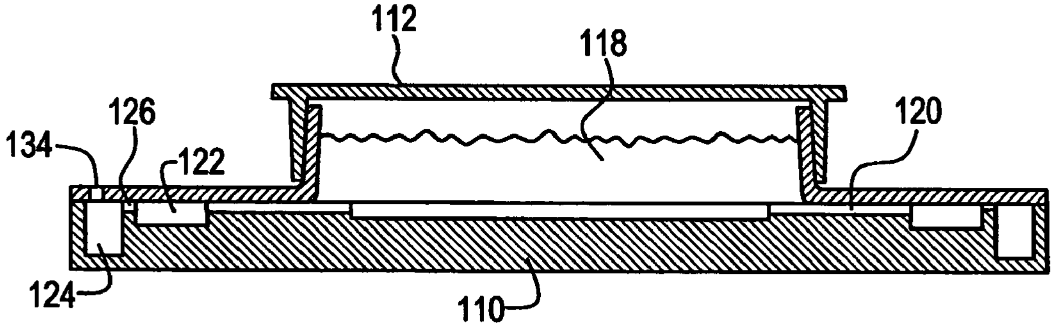
FIG. 8 is a cross-sectional view of the assembled liquid sample testing apparatus of FIG. 1.

As best shown in FIGS. 7 and 8, target wells 122 are deeper than central well 118 and capillary channels 120 and may be formed in various geometrical shapes. For example, target wells 122 as shown in FIG. 4 have a somewhat teardrop or pear-shaped opening having a rounded inner end, straight side walls, are narrower at their juncture with capillary channels 120 and broadening to a rounded outer end. Target wells 122 have a rectangular cross-sectional configuration. Target wells 122 may also be formed in other geometrical configurations. For example, both the opening and cross-sectional profile of target wells 122 may be of different shapes such as, elliptical, circular, or polygonal.

Figure 9:
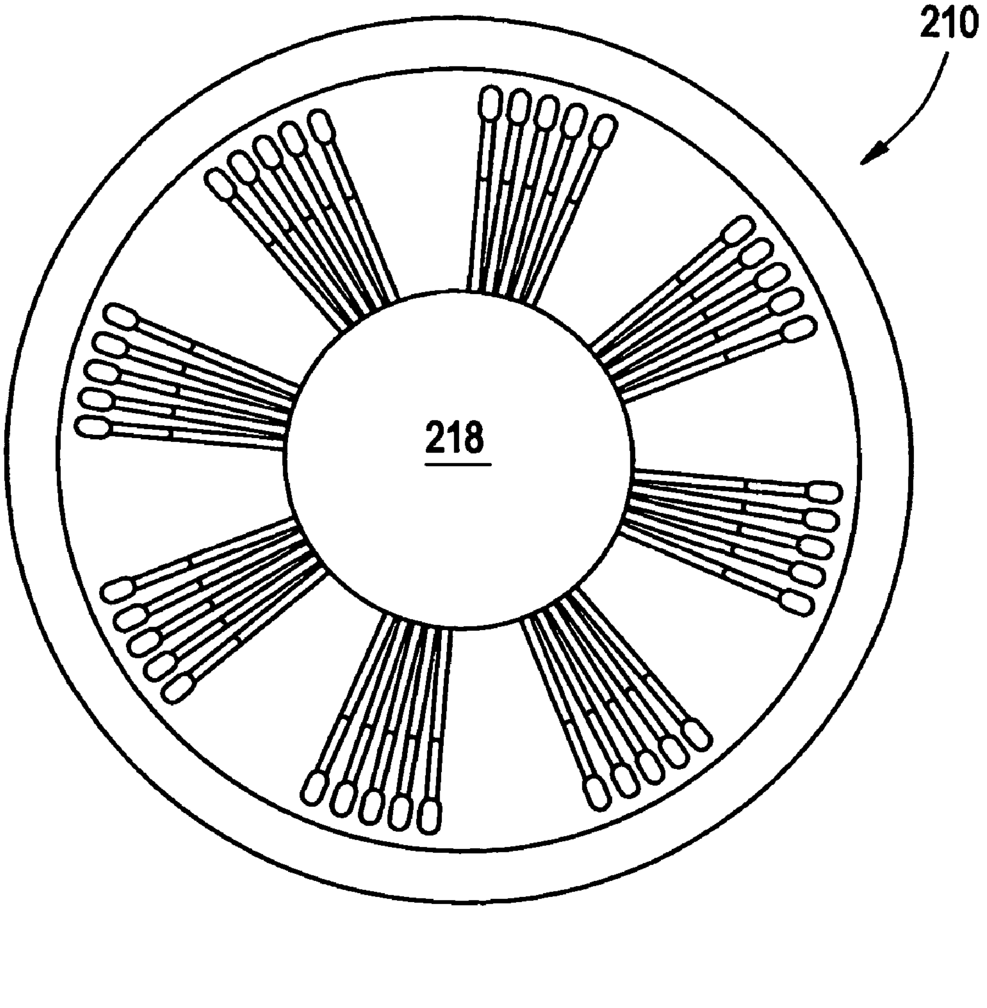
FIG. 9 is a top plan view of an alternative embodiment of a multi-welled base.

As shown in FIG. 6, target wells 122 are arranged in multiple groupings uniformly around base 110. For example, as shown in FIG. 6, target wells 122 are arranged in eight groups of nine wells each for a total of 72 independent target wells to achieve quantification based MPN methods. It is contemplated that different groupings of target wells 122 may be used depending upon the test being performed. For example, as shown in the embodiment of FIG. 9, base 210, which is similar to base 110, has eight groups of five target wells 122 each, fewer target wells 122 may form each grouping in order to visually space each group. Alternatively, it may be desired to have a maximum target wells per disc 100, as shown for example in the embodiment of FIG. 10, wherein base 310 is shown having no distinguishable well groups but rather a continuous series of target wells 122.

Figure 11:
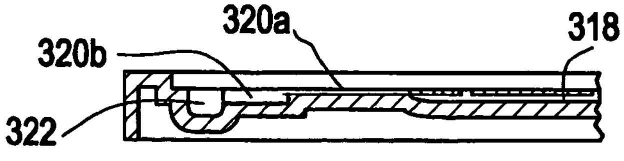
FIG. 11 is a partial cross-sectional view taken along section line 11-11 of FIG. 10.

In each of the base embodiments 210 and 310 there is also illustrated an alternative capillary channel construction from that of the embodiment of FIGS. 1-8. In particular, instead of a single depth capillary channel as shown for channels 120, each of bases 210 and 310 are provided with capillary channels formed to include different sections having different depths. Channel sections furthest away from central wells 218, 318 are of a greater depth than sections closer to central wells 218, 318. As shown in FIG. 11, which is illustrative of base 310, each of capillary channels 320 includes stepped sections 320*a* and 320*b* extending radially away from central well 318 and are in fluid communication with target well 322. Each target well 322 is formed a distance radially away from central well 318 nearer to the periphery of base 310.

Figure 10:
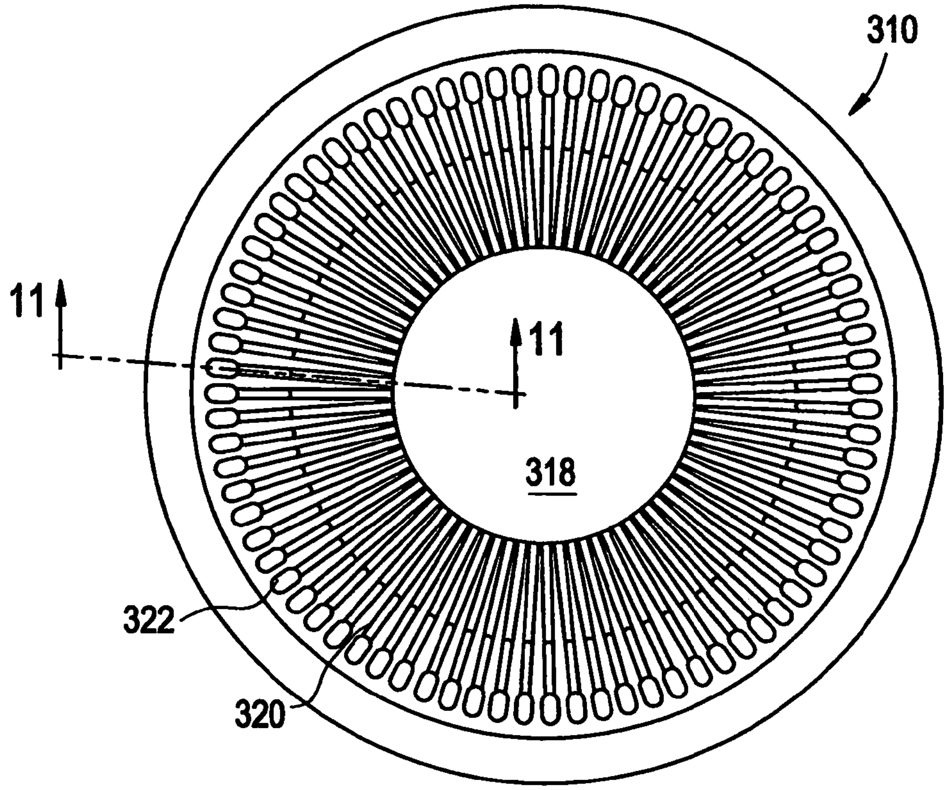
FIG. 10 is a top plan view of a further alternative embodiment of a multi-welled base.

Referring once again to FIGS. 6-8, base 110 further includes an overflow well 124 which is in fluid communication with each of target wells 122 by way of individual run-off channels 126 extending radially outwardly from each target well 122. An absorbent ring 128 is disposed in overflow well 124 to absorb any excess sample liquid flowing into well 124 from each of the individual target wells 122. Alternatively, as shown in the embodiments of FIGS. 9 and 10, base 210, 310 are formed without an overflow well. Excess sample in each of these embodiments is absorbed by an absorbent pad disposed in the cap of each of those embodiments.

A medium to facilitate growth of the target microorganism is placed in the base. Depending on the test being performed different media may be utilized to detect different microorganisms. The choice of testing medium will depend on the biological material to be detected. The testing medium must be a medium, which will detect the presence of the biological material sought to be quantified, and preferably not detect the presence of other biological material likely to be in the medium. It must also be a material, which will cause some visible or otherwise sensible change, such as color change or fluorescence, if the biological material sought to be detected is present in the sample.

In one embodiment, the medium is in a powder form to simplify the overall manufacturing process. The powder may be deposited directly into the sample landing area in the central 118 such that the medium immediately dissolves in the sample when the sample is poured into disc assembly 100. In alternative embodiments, other rapid medium dispersion methods may be utilized, for example, as shown in FIG. 5, a porous solids-containment material, such as medium retention and dispersion bag 130 may be used to retain the powdered medium and prevent movement of the medium during movement of the device, such as during shipping. Medium dispersion bag 130 may function in an analogous manner to that of a tea bag, wherein the material of the bag is porous to permit flow-through of fluids. However, the size of the pores formed in the material making up bag 130 is preferably sized to retain the medium until dissolved by the fluid sample.

Still other rapid medium dispersion devices and techniques are envisioned, for example, quick dissolve tablets, water-permeable seals, etc.

A further alternative approach is to dispense the medium into each target compartment 122 directly. In each of the above-noted medium placement embodiments, the medium forms an integrated part of the device as shipped, thereby eliminating the need for a separate medium package and the separate step of preparing the medium.

Lid 112 is configured and dimensioned to cover base 110 and is sealed to an upper horizontal rim 132 formed along the outer perimeter of base 110 by suitable techniques, for example by ultrasonic welding. A vent hole 134 is formed through lid 112 and is located thereon to be positioned above and in fluid communication with overflow well 124 when lid 112 is secured to base 110. Vent hole 134 is sized to provide sufficient venting when a sample is poured into disc assembly 100 so as to prevent back pressure from impeding the capillary flow action of the sample through capillary channels 120.

Lid 112 is further provided with a collar 136, which extends upwardly from lid 112 and defines an opening 138 through the lid. Cap 114 is configured and dimensioned to fit over collar 136 to form a sliding seal contact therewith. Alternatively, the inside of cap 114 and the outside of collar 136 could be provided with mating threads to facilitate threaded securing of cap 114 to lid 112.

An absorbent pad 140 is configured and dimensioned to be retained within cap 114, for example by a friction fit. In this manner, after a sample has been poured through opening 138 and the cap 112 is placed securely on collar 136, any excessive water sample remaining in central well 118 will be absorbed and retained by pad 140. This will assist in preventing cross-contamination or "cross-talk" between the individual capillary channels 120 and, therefore, individual target wells 122. It is envisioned that the assembly of the various embodiments described herein may be accomplished by way of manual assembly, semi-automatic assembly and fully automated assembly.

Figure 12:
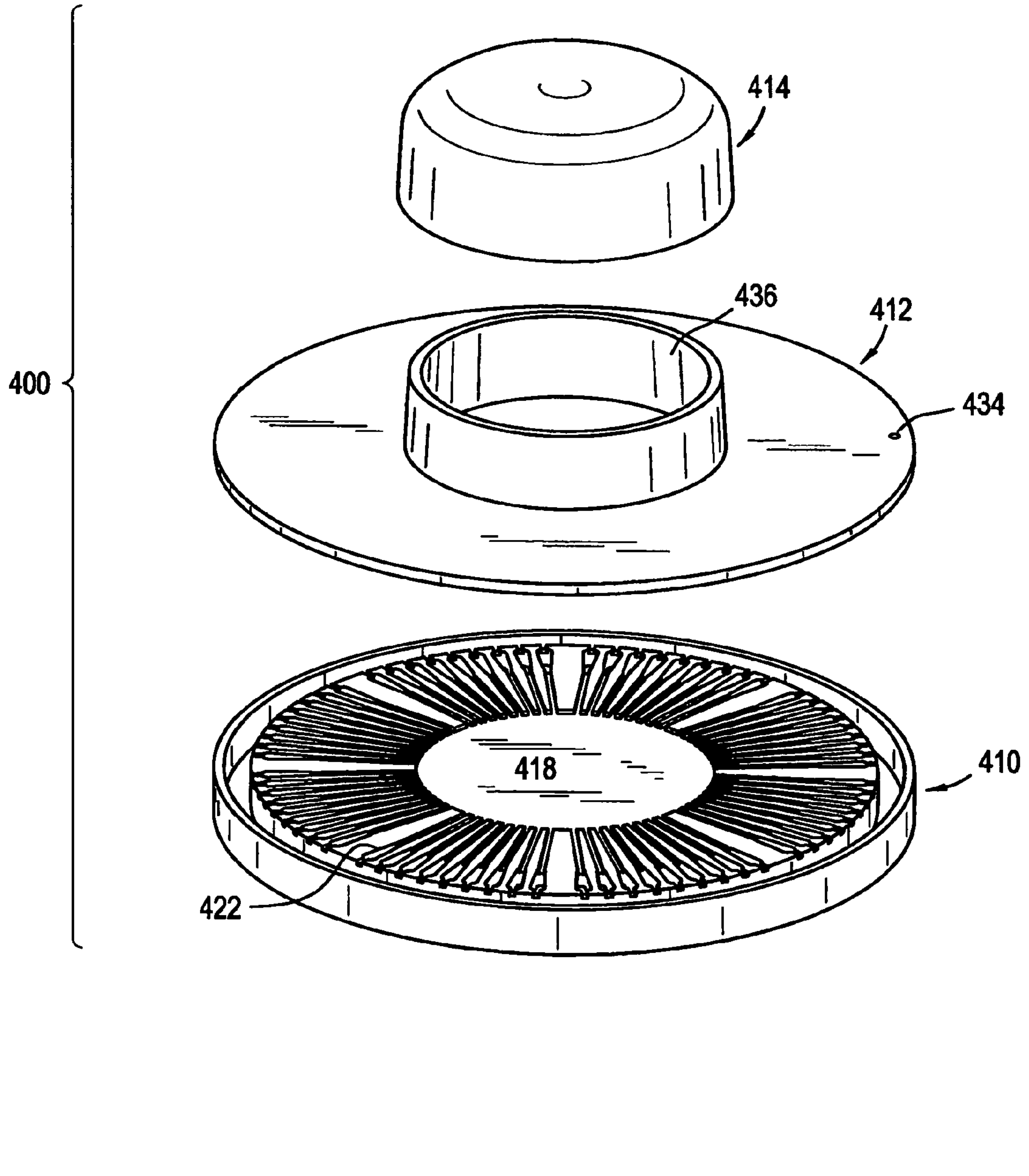
FIG. 12 is a perspective view of another illustrative embodiment of a liquid sample testing apparatus constructed in accordance with the present disclosure.
Figure 13:
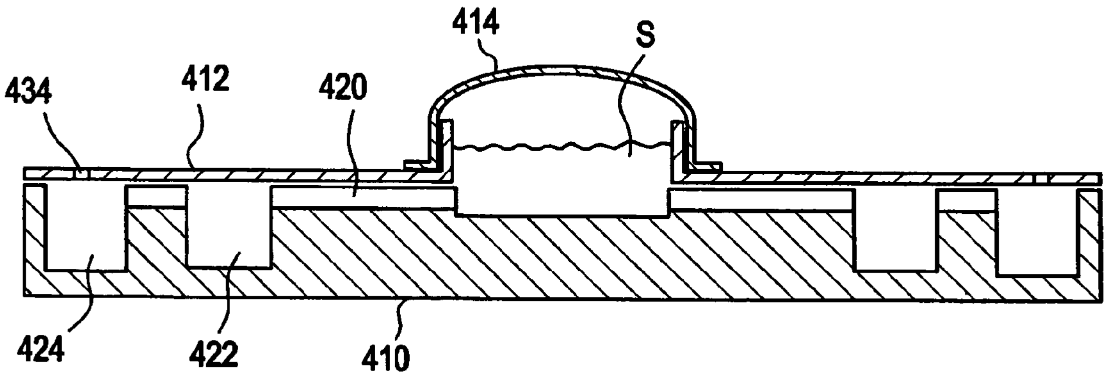
FIG. 13 is a cross-sectional view of the assembled liquid sample testing apparatus of FIG. 12.
Figure 14:
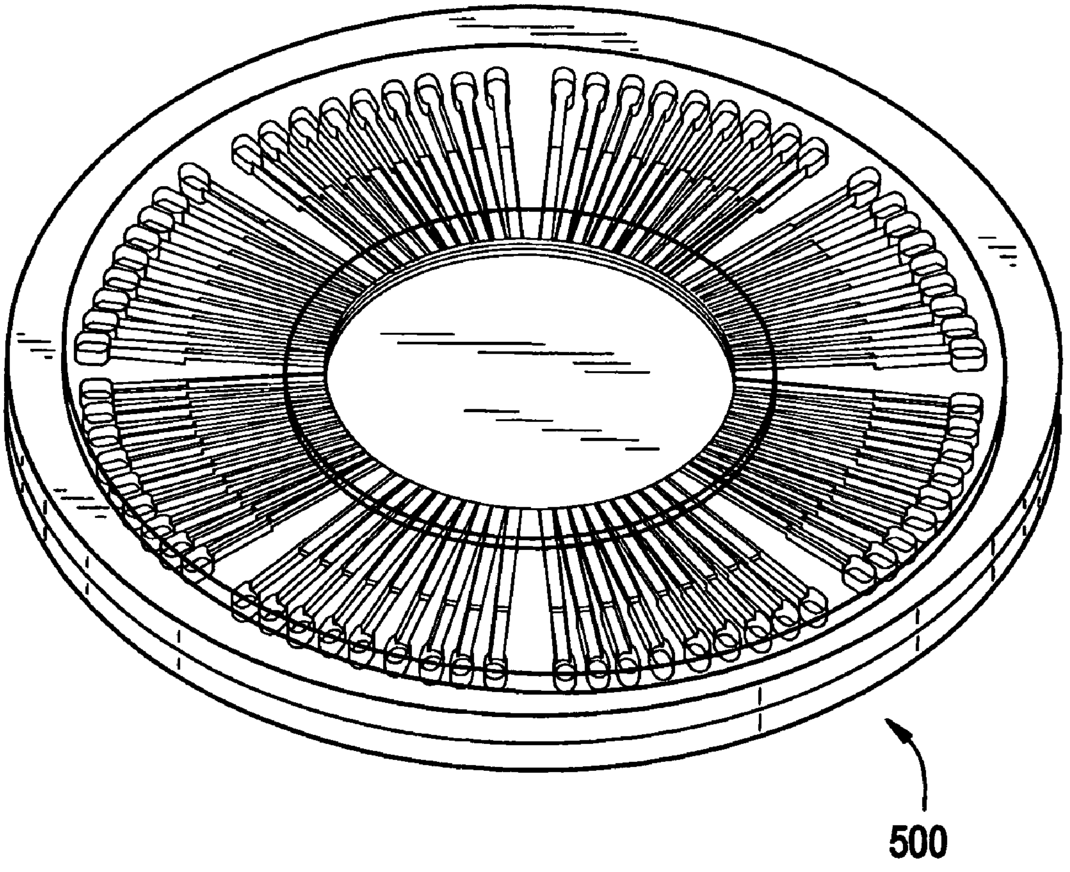
FIG. 14 is a perspective view of another illustrative embodiment of a liquid sample testing apparatus constructed in accordance with the present disclosure.
Figure 15:
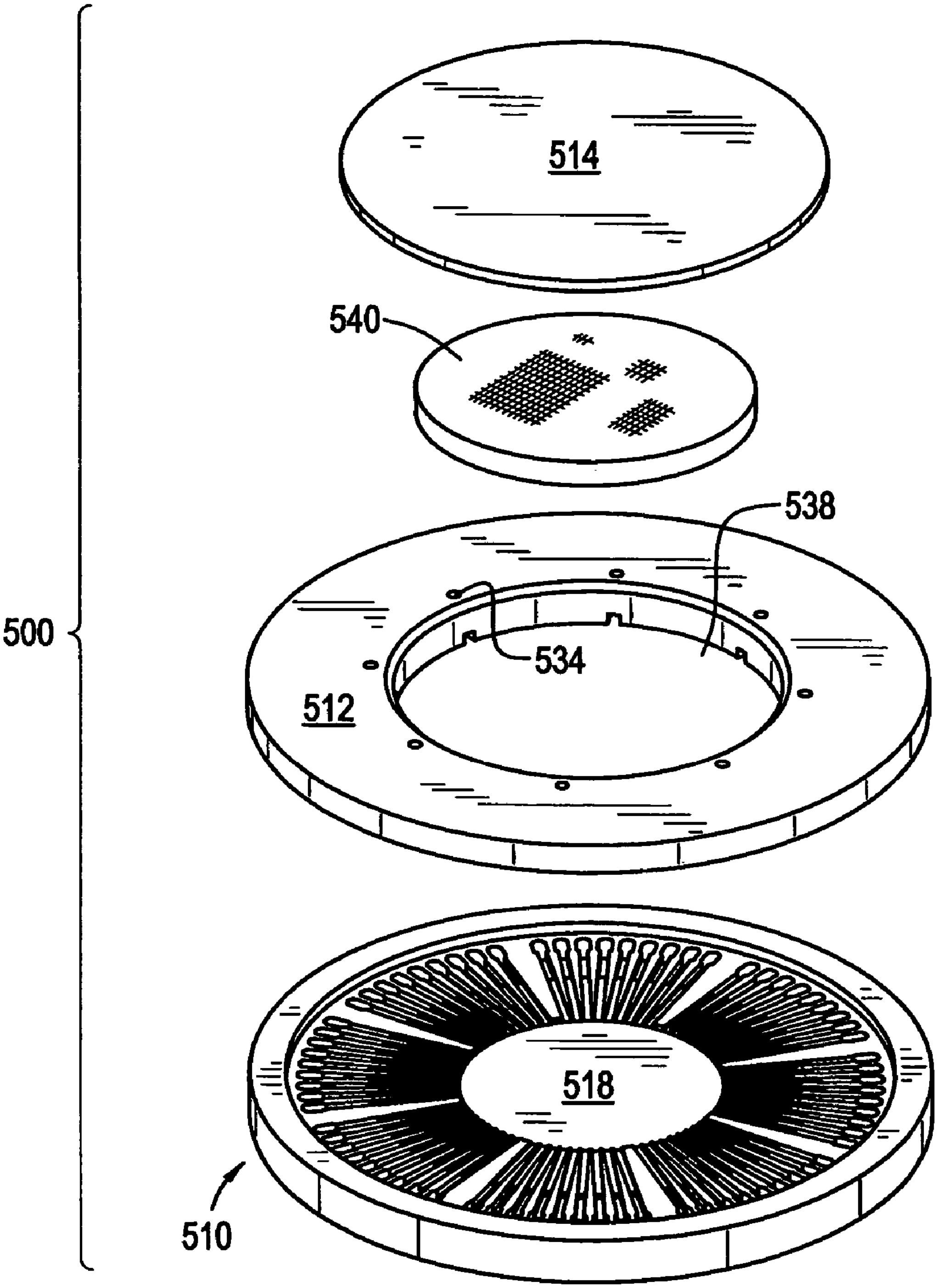
FIG. 15 is a perspective view with parts separated showing the various individual components of the testing apparatus of FIG. 14.

Referring to FIGS. 12 and 13, another illustrative embodiment of a water testing apparatus constructed in accordance with the present disclosure is shown generally as disc assembly 400. For purposes of clarity only the structural components of disc assembly 400 are shown. Some or all of the previously described additional elements may also be incorporated into disc assembly 400 and are not repeated herein. Disc assembly 400 differs from disc assembly 100 in that cap 414 is formed from a pliable material such as rubber to permit the user to push down on the cap after it is placed over the sample "S". This plunging action displaces the volume of air contained below the cap and assists to force the sample through channels 420 and into target wells 422.

Base 410 also illustrates an embodiment wherein legs are not provided so that multiple bases 410 may be placed flat on a horizontal surface. Alternatively, base 410 may be provided with legs as disclosed above for base 110.

Referring now to FIGS. 14-17, a further alternative embodiment of a water sample testing apparatus is shown generally as disc assembly 500. As with the previous disc assembly embodiment 100-400 structure which is similar to that of previous embodiments is labeled similarly except that each element is numbered in the 500 series. Accordingly, those features, which are substantially similar to or the same as previous features noted on the previously described embodiments are labeled herein but are not necessarily separately recited with respect to the embodiment of disc assembly 500.

Figure 16:
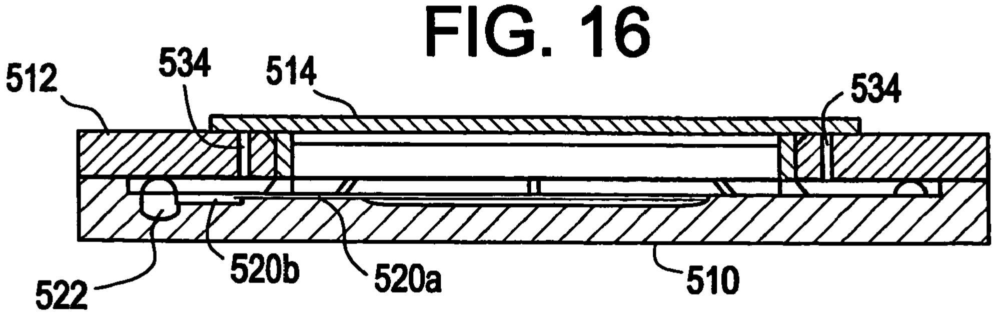
FIG. 16 is a cross-sectional view of the assembled liquid sample testing apparatus testing apparatus of FIG. 14.
Figure 17:
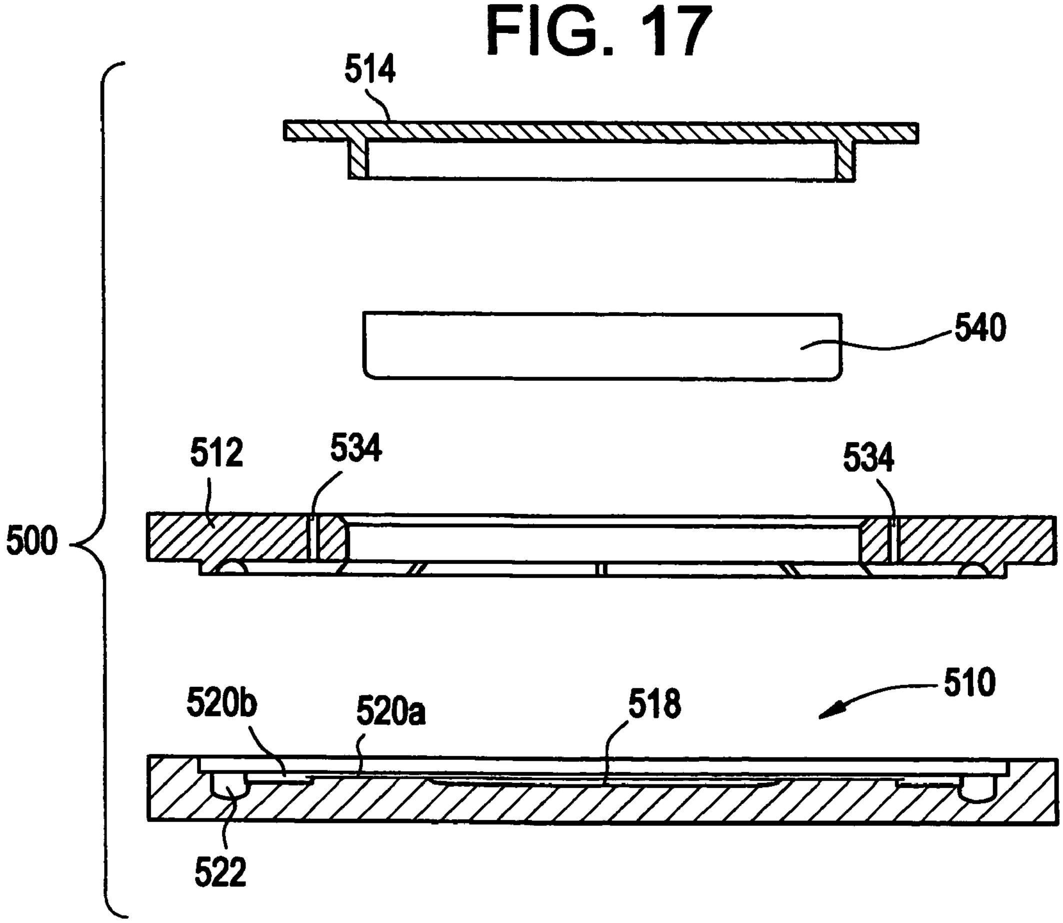
FIG. 17 is a cross-sectional view with parts separated of the liquid sample testing apparatus testing apparatus of FIG. 14.

Lid 512 is formed with fill opening 538 formed therein, but does not include a collar member about the periphery thereof. Instead a series of vent holes are formed in lid 512 close to opening 538. As shown in FIG. 16, vent holes 534 are in fluid communication with capillary channel section 520*b* to provide venting when cap 512 is removed from lid 512. Upon placement of cap 514 in lid 512 vent holes 534 are sealed off to prevent additional infiltration of air during the incubation period. This arrangement is particularly beneficial when it is important to have test conditions that ensure that no additional air is introduced into target wells 522.

Figure 18:
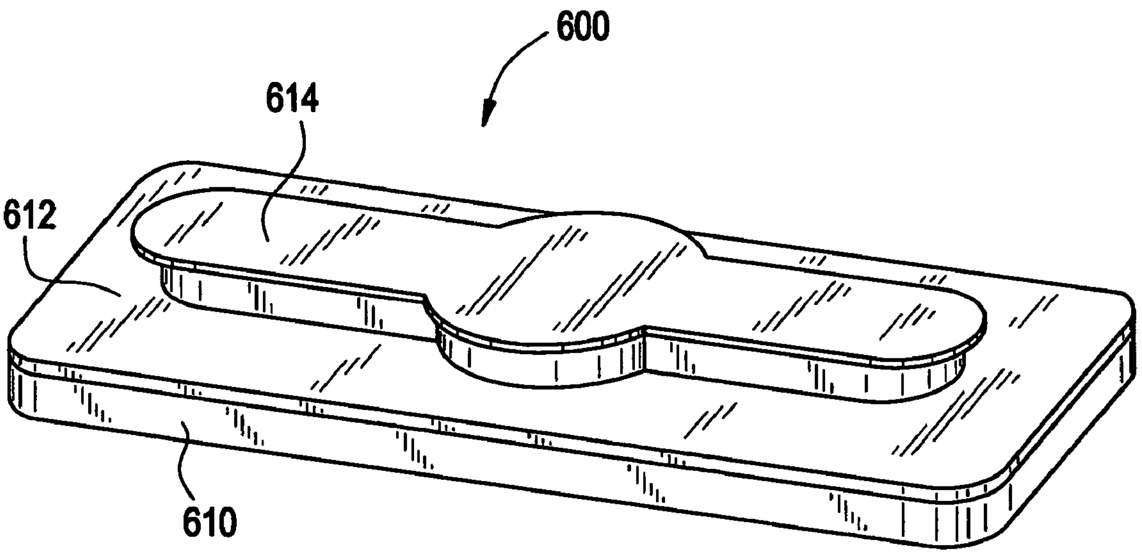
FIG. 18 is a perspective view of a further alternative illustrative embodiment of a liquid sample testing apparatus constructed in accordance with the present disclosure.
Figure 19:
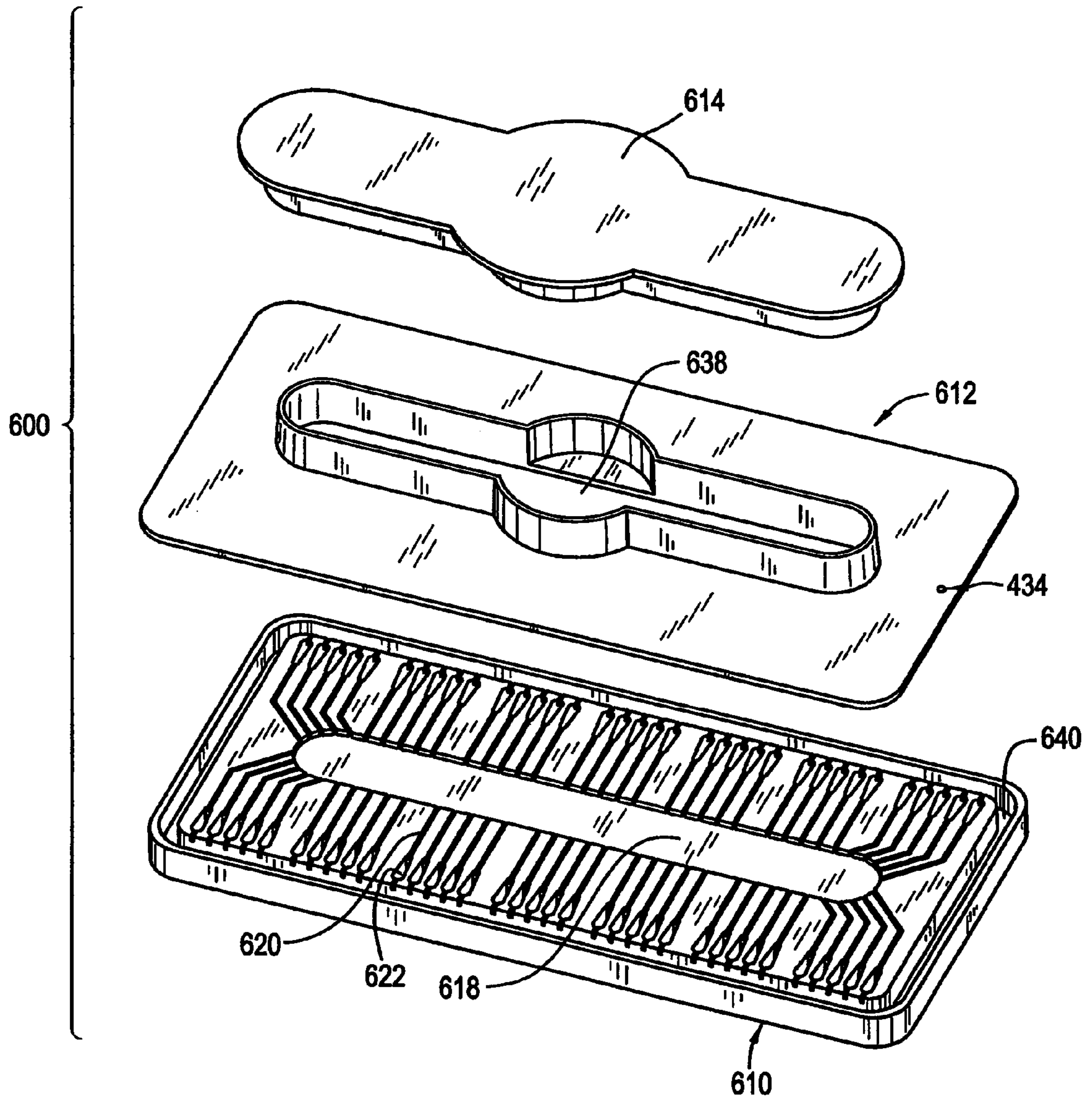
FIG. 19 is a perspective view with parts separated of the testing apparatus of FIG. 18.
Figure 20:
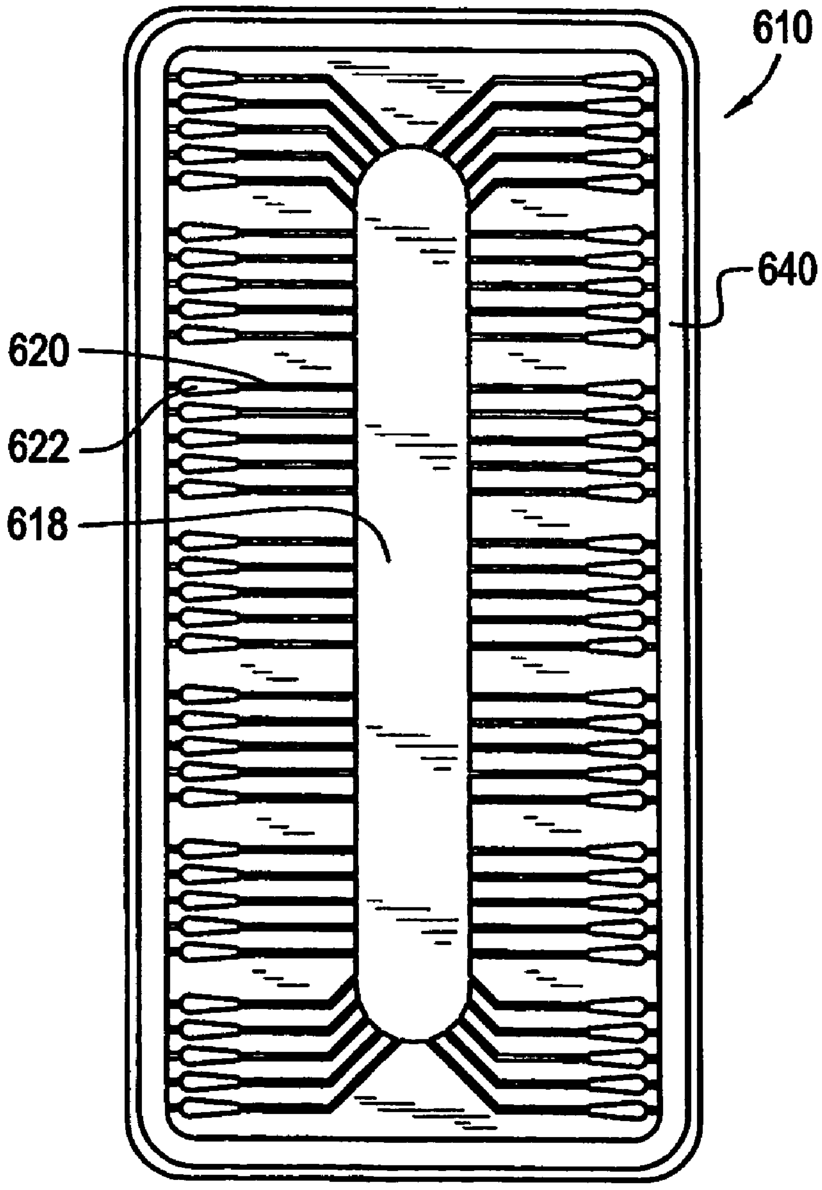
FIG. 20 is a top plan view of a base of the liquid sample testing apparatus of FIG. 18.

Referring to FIGS. 18-20, a further alternative embodiment of the presently disclosed water sample testing apparatus is shown generally as test device 600, which is substantially similar to the previous embodiments in many respects. The principle difference of test device 600 is that it is formed in a generally rectangular configuration. In all other aspects, test device 600 is similar to the previously described embodiments and may be constructed to include the various alternative features previously described herein.

The method of using each of the above-described embodiments is substantially similar and will now be described. Where differences between embodiments exist, they will be noted. Briefly, to conduct a liquefied sample test, such as a water sample test, a user removes the cap and pours approximately 1 ml to approximately 5 ml of water sample into the center well, replaces the cap, inverts the test device once to absorb excessive sample left in the center well, and incubates the test device at the required temperature and for the time required by the particular test. Results are obtained by the enumeration of positive targets and comparing enumerated positives to a MPN table.

When the sample is poured in to the center well, the powder medium is dissolved upon contact with the water sample to achieve a proper sample-medium mixture. When the height of the sample in the center well reaches the height of the capillary channels, the sample-media mixture flows to the wells located at the outer edge of the test device.

The device may be left in the inverted position or may be returned to the original upright position for the incubation period. As previously noted, for those embodiments which facilitate it, where multiple tests are to be conducted simultaneously, the individual devices may be stacked upon each other due to the uniquely advantageous structure of the base with the stepped legs formed thereon.

Figure 21:
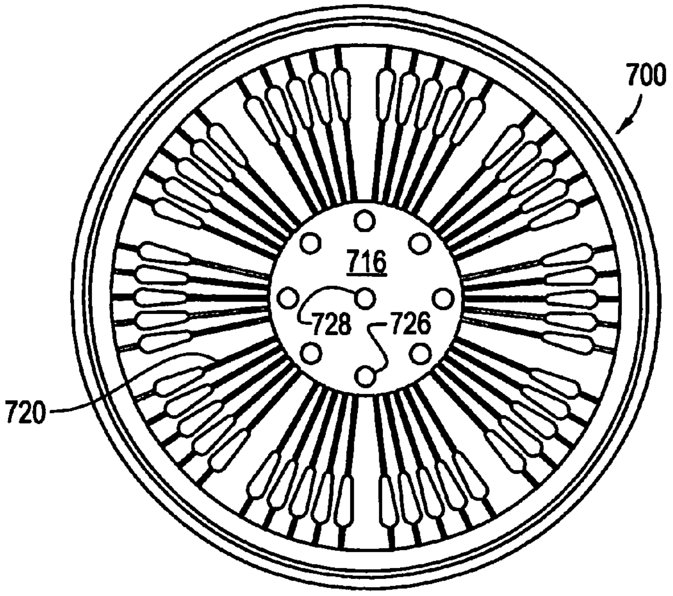
FIG. 21 is a perspective view of a further alternative illustrative embodiment of a liquid sample testing apparatus constructed in accordance with the present disclosure.
Figure 22:
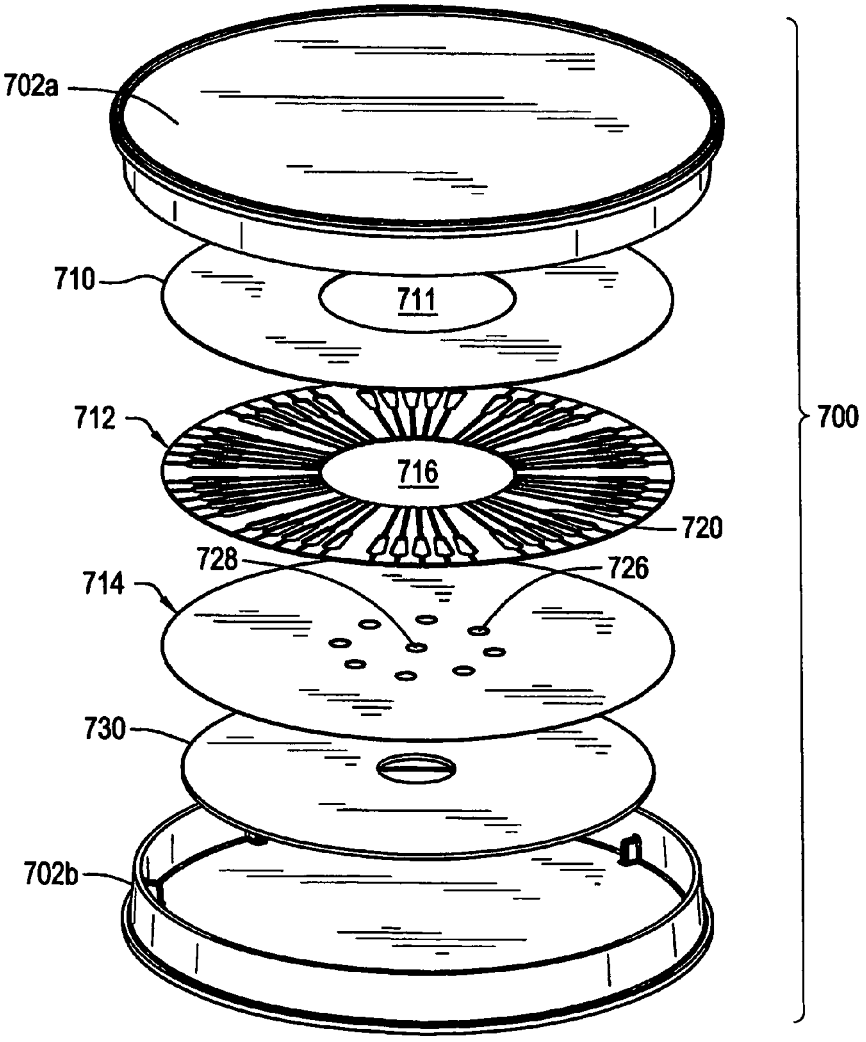
FIG. 22 is a perspective view with parts separated of the liquid sample testing apparatus of FIG. 21.
Figure 23:
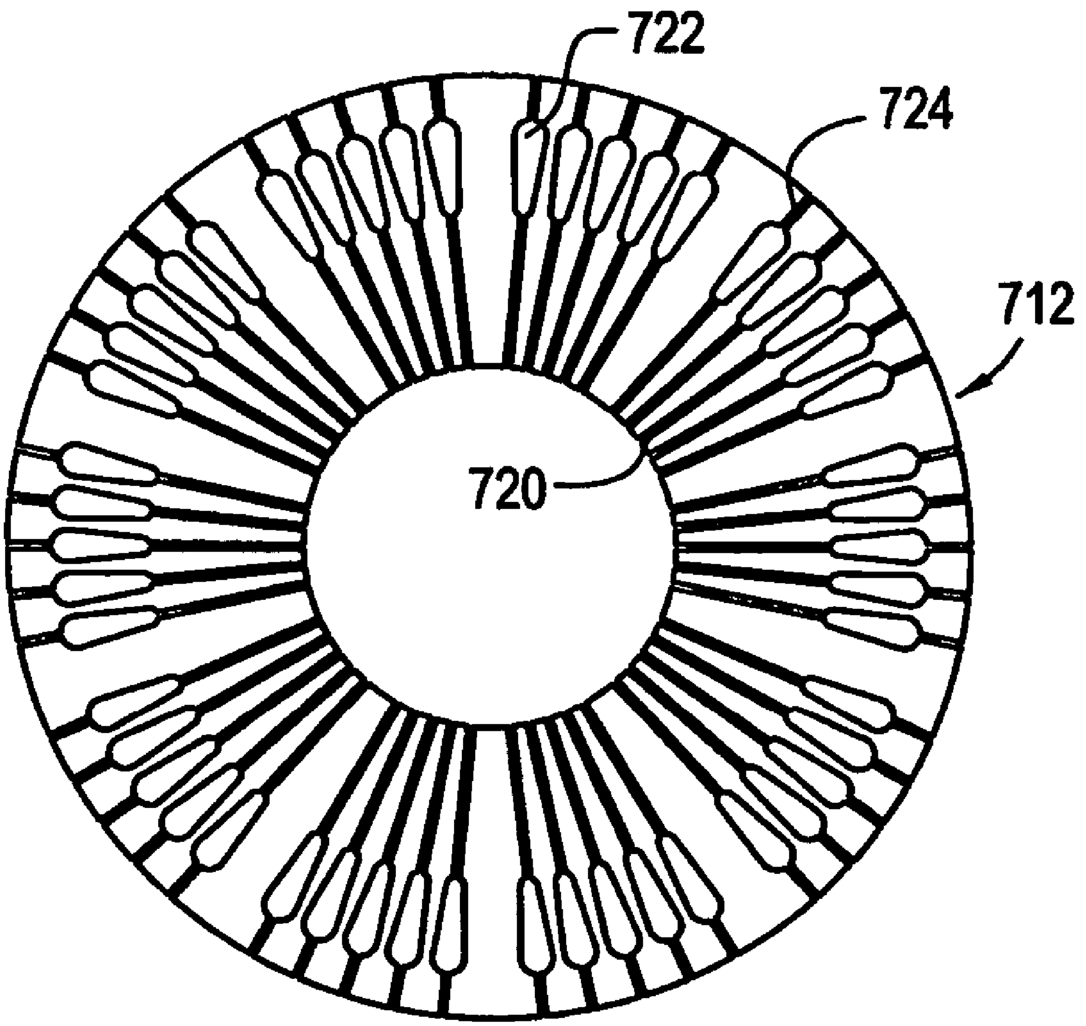
FIG. 23 is a top plan view of a frame element which forms capillary channels of the testing apparatus of FIG. 21.

FIGS. 21-23 illustrate a further alternative embodiment of a liquid sample testing apparatus for the quantification of target microorganisms, which is shown generally as test device 700. Briefly the operational portion of test device 700 includes a multiple layer assembly of plastic films which are held together as a unit, for example by a transfer adhesive and are enclosed in a hydrophobic container such as a two-part transparent dish having a top portion 702*a* which fits over a bottom portion 702*b*. The multiple-layer film assembly includes a top hydrophilic layer 710, a hydrophobic frame 712 which includes at least one capillary channel 720 formed therein, and a plastic backing layer 714.

Preferably, top layer 710 is made of clear polyester (PE) material with a hydrophilic surface to facilitate passage of the liquid sample being tested through top layer 710 and into hydrophobic frame 712. Alternatively, top layer 710 may be made from any other clear plastic material with a hydrophilic surface. Furthermore, the top layer 710 can be hydrophilic and have a heat or pressure sensitive adhesive coated on the same side facing the frame 712. This configuration can eliminate the need to use a transfer adhesive or other means of bonding to put the two parts together.

Hydrophobic frame 712, which forms the capillary channel structure, is preferably made from material selected from the group consisting of polystyrene, polyester, and PETG. A sample-landing zone 716 is defined in the central portion of frame 712. Capillary channels 720 are formed in hydrophobic frame 712 and are enclosed from top and bottom when top layer 710 and plastic backing layer 714 are adhered to hydrophobic frame 712, for example by a transfer adhesive. Each capillary channel is in fluid communication with the sample-landing zone 716 and is adapted to partition liquid sample from sample-landing zone 716 to the recessed compartment. Capillary channels 720 may be formed in various clustered arrangements or in a continuous arrangement as described with respect to the previous embodiments.

As shown in FIG. 23, fifty capillary channels 720 are arranged in groups of five. Each of capillary channels 720 includes a reaction well 722 are formed in hydrophobic frame 712. The capillary channels 720 and reaction wells 722 may be configured and dimensioned as shown or in any of the previously described configurations and dimensions set forth with respect to the other embodiments illustrated and described herein.

Reaction wells 722 are formed to include at least one recessed compartment, which is in fluid communication with a venting slot 724 disposed radially outwardly therefrom to facilitate the capillary flow. Each reaction well 722 is configured and dimensioned to hold an aliquot of sample/medium mixture for the detection of the targeted biological material.

The plastic backing layer 714 is hydrophobic plastic layer. It is preferably made from polyester or other similar material. Plastic backing layer 714 includes a series of holes 726 formed therethrough, each hole being preferably spaced radially such that upon assembly of the layers, holes 726 are positioned one each, in between the groups of capillary channels 720 (see FIG. 24). A central hole 728 is formed to align centrally with the sample-landing zone 716. Together holes 726 and 728 facilitate passage of excess sample through to the bottom of device 700.

In an alternative embodiment, the device may further include an absorbent pad 730, which is positioned below the multi-layer plastic assembly inside bottom disc portion 702*a* to absorb any excess liquid sample. The absorbent material may be a die cut polyester foam, polyether foam, cotton, or a cellulose acetate or other suitable absorbent material. The absorbent pad containing excessive liquid samples also acts as a humidifying source to prevent the assay in the assembly 700 from drying out during incubation.

In use, the top disc portion 702*a* is removed from device 700 and an inoculating volume of approximately 3.5 ml of liquid sample is introduced into sample landing zone 716 and top portion of disc 702*a* is replaced to close device 700. The total time for introduction of the sample should be approximately 5 seconds. The sample fills the landing zone 716 and is drawn by capillary action into capillary channels 720 and fills each of reaction wells 722. Excess sample is absorbed by pad 730 as it either travels through holes 726, 728 or through venting slots 724.

Figure 24:
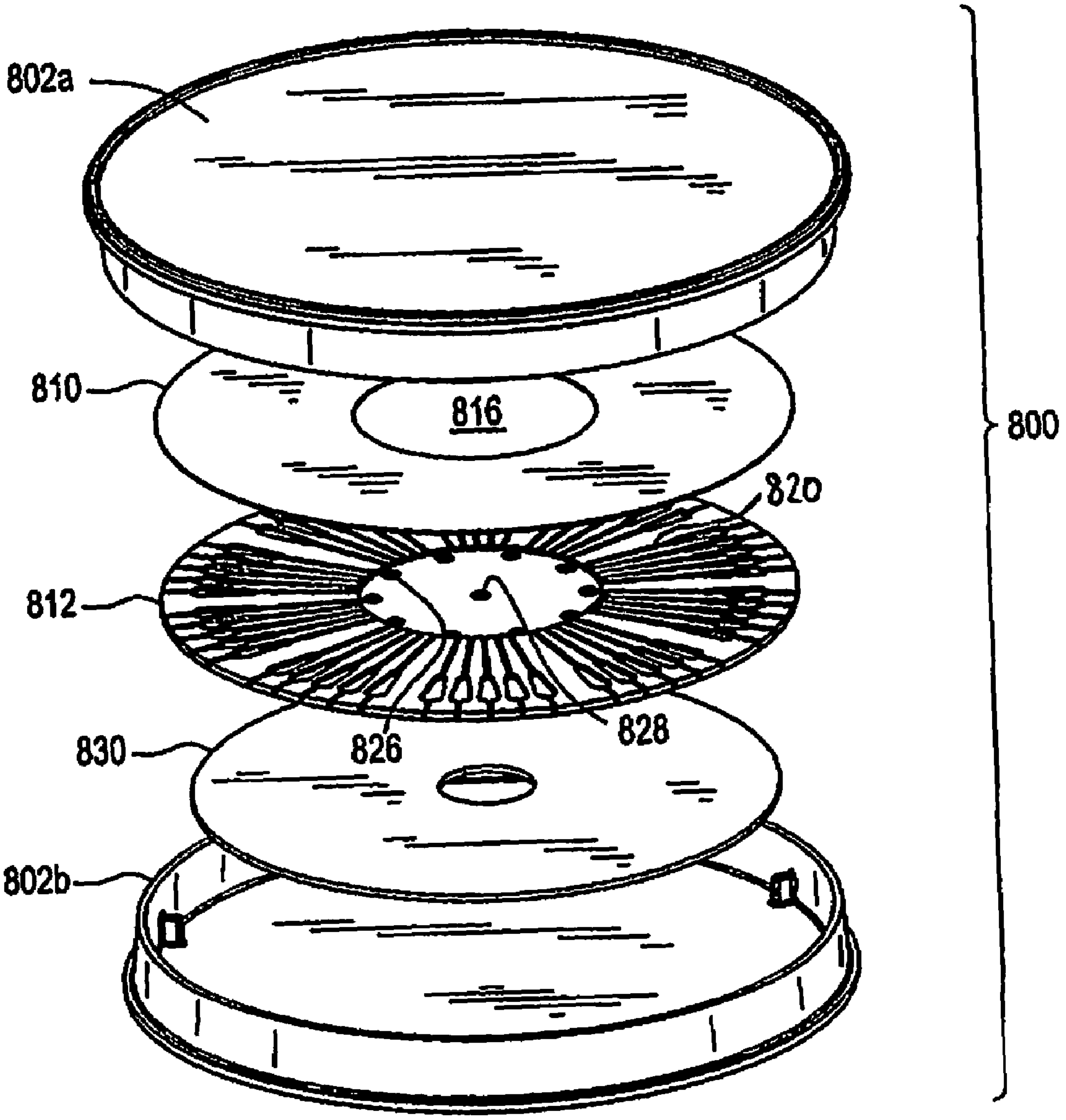
FIG. 24 is a perspective view of a further alternative illustrative embodiment of a liquid sample testing apparatus constructed in accordance with the present disclosure.

FIG. 24 illustrates a further alternative embodiment of a liquid sample testing apparatus for the quantification of target microorganisms, which is shown generally as test device 800. The operational portion of test device 800 is similar to that of test device 700 in that it also includes a multiple layer assembly of plastic films, which are held together as a unit, and are enclosed in a hydrophobic container such as a two-part transparent dish having a top portion 802*a*, which fits over a bottom portion 802*b*. The multiple-layer film assembly includes a top hydrophilic layer 810 having a sample receiving hole 816 formed therethrough, a hydrophobic frame 812 which includes at least one capillary channel 820 formed therein, and an absorbent pad backing layer 830. Hydrophobic frame 812 may be formed by suitable techniques such as injection molding or heat stamping. Furthermore, the top layer 810 can be both hydrophilic and heat or pressure-sensitive achieve coated on the same side facing the frame 812. This configuration can eliminate the usage of transfer achieve or other means of bonding to put the two parts together.

Test device 800 does not include, however, a backing layer like plastic backing layer 714 of test device 700. Instead, vent holes 826 and central hole 828 are formed in the central region of hydrophobic frame 812. As with the various previous embodiments, capillary channels 820 may be formed in various clustered arrangements or in a continuous arrangement as described with respect to the previous embodiments. The use of test device is the same as that for test device 700 and will not be addressed in detail again. Furthermore, the top layer 810 can be both hydrophilic and heat or pressure-sensitive achieve coated on the same side facing the frame 812. This configuration can eliminate the usage of transfer achieve or other means of bonding to put the two parts together.

Figure 25:
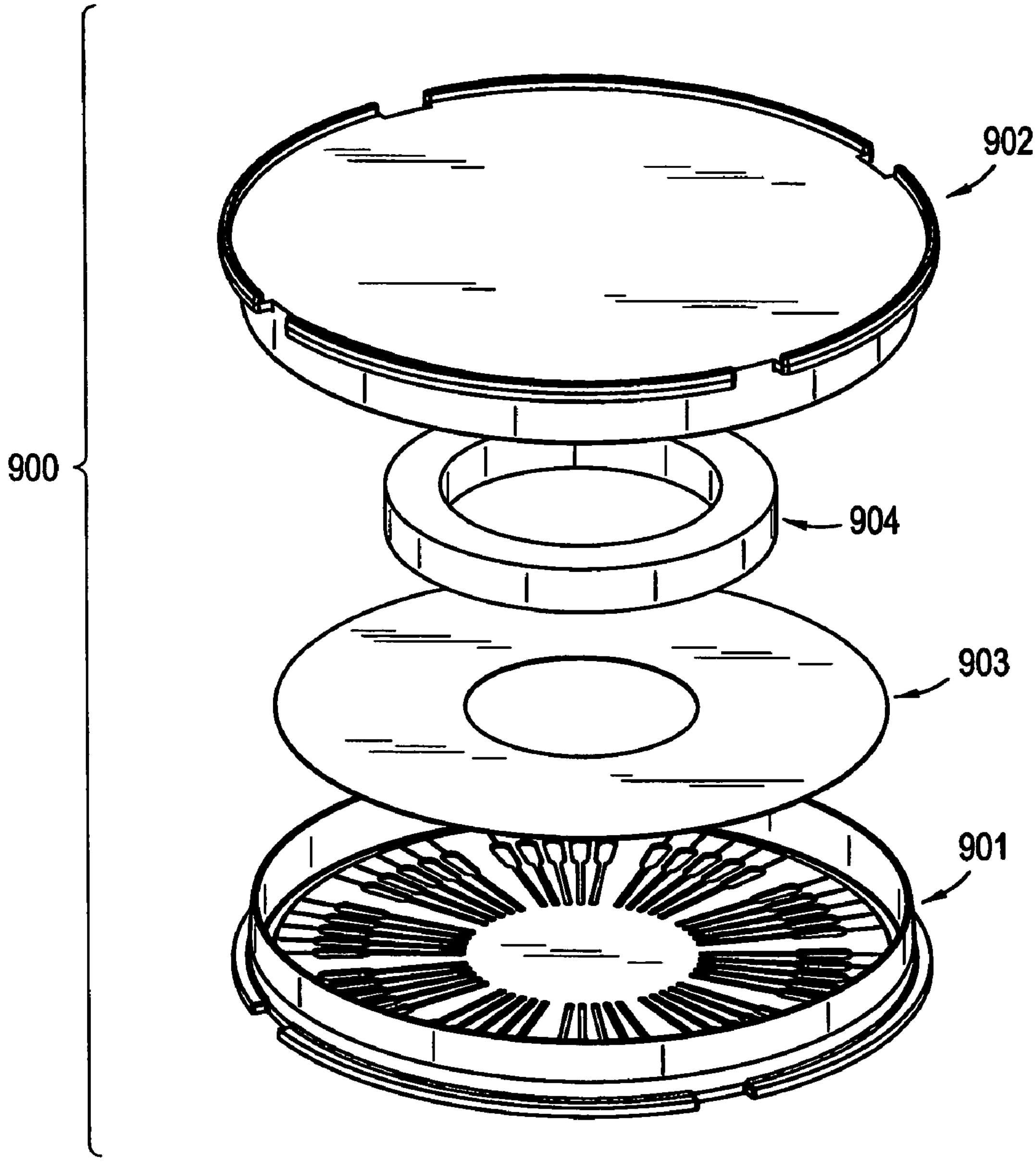
FIG. 25 is a perspective view of a further alternative illustrative embodiment of a liquid sample testing apparatus constructed in accordance with the present disclosure.
Figure 26:
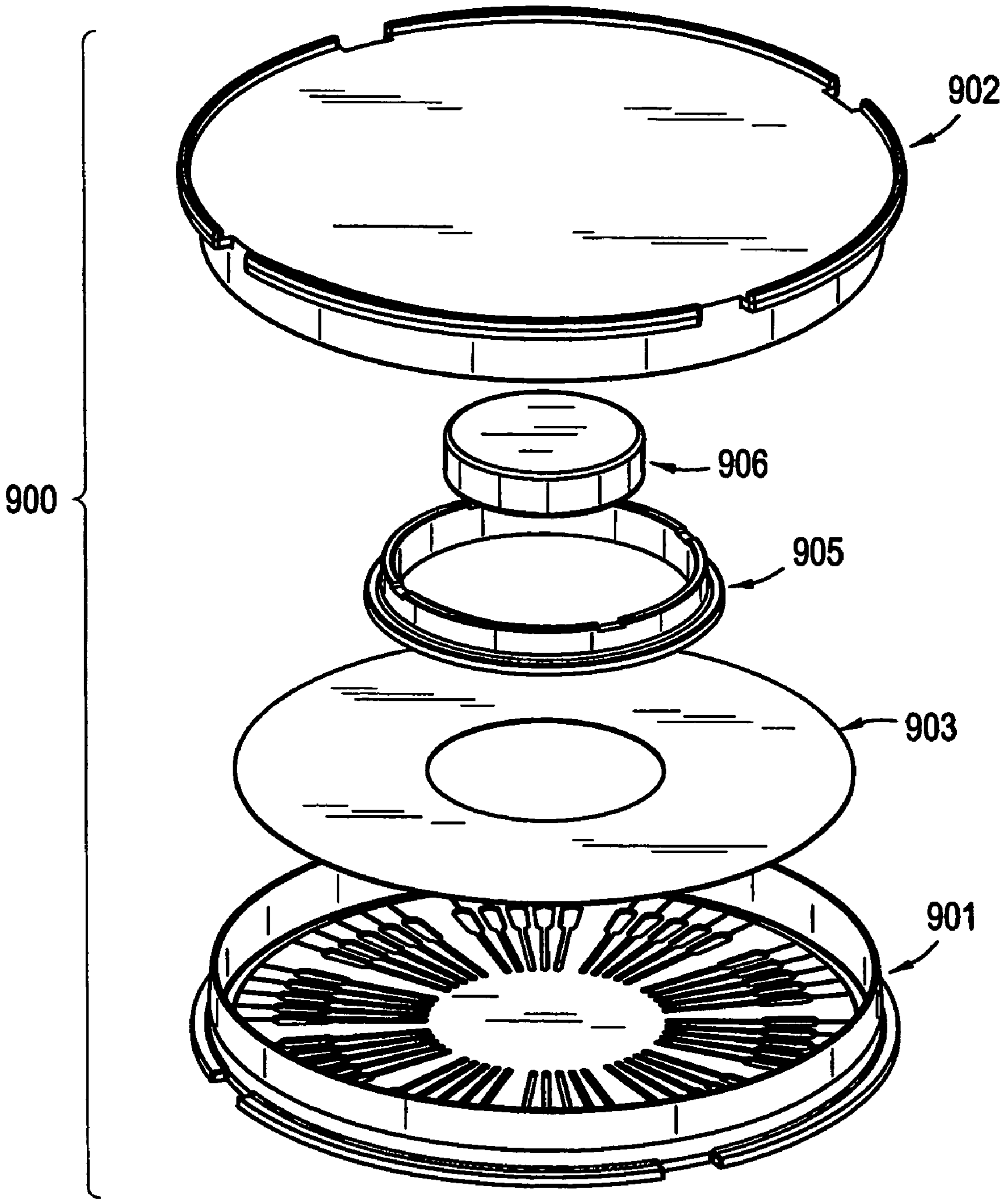
FIG. 26 is a perspective view of yet another alternative illustrative embodiment of a liquid sample testing apparatus constructed in accordance with the present disclosure.

FIGS. 25-26 illustrate a further alternative embodiment of a liquid sample testing apparatus for the quantification of target microorganisms, which is shown generally as test device 900. The operational portion of test device 900 includes the distribution channels and recessed compartments molded directly onto a bottom half 901 of test device 900 through the injection mold technique. As with the various previous embodiments, capillary channels and target reaction compartments are formed by placing a plastic film 903 on top of bottom half 901 of device 900. Plastic film 903 can have either a heat or a pressure-sensitive adhesive coated on the same side facing bottom half 901 of device 900. An absorbent ring 904 may be attached on top of plastic film 903 to absorb the excess liquid or liquefied sample/medium mixture. Alternatively, as shown in FIG. 26, a plastic ring 905 may be attached on top of plastic film 903 to contain the liquid sample or liquefied sample/medium mixture before distributing into the capillary channels and target reaction compartments through the capillary action. In addition, as seen in FIG. 26, an absorbent pad 906 is attached on a top half 902 of device 900 to absorb the excess liquid or liquefied sample/medium mixture. The use of test device 900 is the same as that for previous embodiments and will not be addressed in detail again.

EXAMPLE 1

Bacterial Detection and Enumeration Device for Heterotrophic Bacteria in Water The following is an example of how the present invention provides a method of detecting and enumerating heterotrophic bacteria in water samples. The device used in this assay is constructed according to the drawing illustrated in FIG. 26. The medium of Townsend and Chen (U.S. Pat. Nos. 6,387,650 and 6,472,167) is provided and deposited in the capillary channels and reaction compartments. The medium includes the following components: a source of amino acids and nitrogen mixture (2.5 gram/liter); a source of vitamin mixtures (1.5 gram/liter); sodium pyruvate (0.3 gram/liter); magnesium sulfate (0.5 gram/liter); fast green dye (0.002 gram/liter); buffer components (4.4 gram/liter); and a mixture of enzyme substrates (0.105 gram/liter).

The results of this example were evaluated against an International Standard Method ISO 6222 (Water Quality—Enumeration of Culturable Micro-organisms—Colony Count by Inoculation in a Nutrient Agar Culture Medium). Data were analyzed using the statistical method described in the ISO Method 17994 (Water Quality—Criteria for establishing the equivalency of two microbiological methods). Results are reported in Table I, below. A total of 368 water samples were analyzed and incubated at 37° C. for 48 hours and a total of 339 water samples were incubated 22° C. for 72 hours. An aliquot of 3.5 mL of each water sample was added to the sample-landing area of the device and was automatically distributed through capillary action into all the reaction compartments within few seconds. The device was then incubated at 37° C. for 48 hrs or 22° C. for 72 hrs. Bacterial concentrations in the water sample were determined by examining the number of reaction compartments exhibiting fluorescent signal under a UV lamp ($366_{nm}$). The number of bacteria present in the sample was then determined based on MPN statistics. The statistical analysis of the data based on ISO Method 17994 (Water Quality—Criteria for establishing the equivalency of two microbiological methods) is set forth in Table I.

TABLE I

ISO Method 17994 Statistical Analysis Comparison between the present invention and ISO Method 6222

| | 37° C. for 48 hrs | 22° C. for 72 hrs |
|---|---|---|
| N | 368 | 339 |
| Mean % RD | 9.9 | 16.3 |
| U | 10.3 | 12.1 |
| LO | −0.5 | 4.2 |
| HI | 20.2 | 28.3 |

N = Number of Samples
RD (Relative Difference) means the difference between two results A (invention) and B (ISO Method 6222) measured in the relative (natural logarithmic) scale. The value of RD is expressed in percent according to RD % = 100 · [ln (A) − ln (B)].
U (Expanded Uncertainty) is derived from the standard uncertainty of the mean by using the coverage factor κ = 2. To evaluate the result of the comparison the "confidence interval" of the expanded uncertainty around the mean is calculated by computing the limits: LO (Lower Limit) = Mean % RD − U and HI (Upper Limit) = Mean % RD + U. It is desirable to achieve an average performance that is either quantitatively equivalent or higher than the reference method. In such cases, the "One-sided Evaluation" method is used and two methods are determined to be "no different" when −10 ≦ LO ≦ 0 and HI > 0.
When LO is greater than zero, it means that the method of the present invention is more sensitive than the reference method.

The results reported in Table I indicate that the device and method according to the present invention can detect and enumerate heterotrophic bacteria in water samples and is equivalent or better than the standard reference method.

EXAMPLE II

Bacterial Detection and Enumeration Device for *Enterococcus* Bacteria

The following is another example of detecting and enumerating microorganisms using the present invention. The device used in this assay is constructed according to the drawing illustrated in FIG. 26. The medium of U.S. Pat. No. 5,620,865 (Chen, et al., which is practiced by IDEXX's commercial Enterolert™ medium, a medium for the detection of *Enterococcus* bacteria in a sample) is provided and deposited in the capillary channels and reaction compartments. A known level, as determined by the Typicase Soy Agar supplemented with 5% sheep blood, of *Enterococcus feacalis* ATCC 35667 was inoculated into a device of this invention (Table II). Results indicated that the concentration of *E. faecalis* ATCC 35667 determined by the FIG. 26 device is statistically equivalent to those determined by the TSA with 5% sheep blood plate count method.

TABLE II

| | TSA/5% Sheep Blood | FIG. 26 Device |
|---|---|---|
| Replicate 1 | 22 | 24.5 |
| Replicate 2 | 16 | 13.5 |
| Replicate 3 | 14 | 29.3 |
| Replicate 4 | 16 | 17.1 |
| Replicate 5 | 22 | 15.5 |
| Average | 18 | 20.1 |
| Standard Deviation | 3.7 | 6.7 |

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A method of partitioning a liquefied sample for determining an amount of microorganisms in a liquefied sample comprising:

providing a device including:

a bottom member having at least one discrete reaction compartment;

a sample receiving well disposed in the bottom member;

a top member disposed adjacent the bottom member;

at least one channel member at least partially defined by at least one of the top and bottom members, each channel member having a first end portion in direct fluid communication with the sample receiving well and a second end portion in direct fluid communication with a discrete reaction compartment;

an overflow well in direct fluid communication with the discrete reaction compartment; and a vent opening;

introducing a portion of the liquefied sample to the sample receiving well, whereby capillary action assists in causing a portion of the liquefied sample to travel from the first end portion to the second end portion of the at least one channel member, wherein the liquefied sample is subsequently partitioned into the discrete reaction compartment and at least a portion of the liquefied sample is caused to remain in the reaction compartment; and wherein excess liquefied sample is caused to be deposited in the overflow well; and analyzing microbial concentrations in the liquefied sample.

2. The method according to claim 1, wherein the liquefied sample is mixed with microbiological media prior to introducing the liquefied sample to the device.

3. The method according to claim 1, wherein the device has microbiological media associated therewith in a manner that allows mixing with the liquefied sample upon the step of introducing the liquefied sample to the device.

4. A method for performing a liquid sample testing comprising the steps of:

providing a liquid sample testing device including:

a lid; and a base operatively engagable with the lid to form an integrated unit, the base including:

a sample receiving well having a depth;

a plurality of capillary channels extending radially from the sample receiving well, each capillary channel having a depth which is less than the depth of the sample receiving well and being in direct fluid communication with the sample receiving well;

a target well formed at the end of each capillary channel, each target well having a depth greater than the depth of the capillary channel and being in direct fluid communication with the at least one capillary channel, the target well being configured and dimensioned for determining the presence and amount of microorganisms in the liquefied sample; and an overflow well, the overflow well being in direct fluid communication with each target well via a run-off channel extending between each target well and the overflow well;

providing a medium carried in at least one of the sample receiving well and each discrete target well;

introducing a quantity of a liquid sample into the sample receiving well, wherein capillary action assists in causing the liquid sample to travel from the sample receiving well into the at least one capillary channel wherein the liquid sample is subsequently partitioned into the discrete target well and at least a portion of the liquefied sample is caused to remain in the discrete target well for determining the presence and amount of microorganisms in the liquefied sample and wherein excess liquefied sample is caused to be deposited in the overflow well;

incubating the testing device at a predetermined temperature for a predetermined amount of time for a particular test; and analyzing microbial concentrations in the liquefied sample.

5. The method according to claim 4, wherein the step of introducing a quantity of the liquid sample includes introducing approximately 1 ml to approximately 5 ml of liquid sample to the sample receiving well.

6. The method according to claim 4, further including the steps of:

counting positive targets; and comparing the positive targets to an MPN table.

7. The method according to claim 4, wherein the device further includes a cap configured to sealingly close an opening formed in the lid, wherein the method further includes:

introducing the liquid sample to the sample receiving well through the opening in the lid; and placing the cap on the lid to close the opening.

8. The method according to claim 7, wherein the device includes an absorbent material disposed in the cap, and wherein the method further includes the step of inverting the device after the cap has been placed on the lid.

9. A method of partitioning a liquefied sample for determining an amount of microorganisms in a liquefied sample comprising:

providing a device including:

a bottom member having at least one discrete reaction compartment;

a top member disposed adjacent the bottom member;

a sample receiving well positioned in a central region relative to the top and bottom members;

at least one channel member at least partially defined by at least one of the top and bottom members, each channel member having a first end portion in direct fluid communication with the sample receiving well and a second end portion in direct fluid communication with a discrete reaction compartment; the at least one channel member extending radially outward from the central region;

an overflow well in direct fluid communication with the discrete reaction compartments; and a vent opening;

introducing a portion of the liquefied sample to the sample receiving well, whereby capillary action assists in causing a portion of the liquefied sample to travel from the first end portion to the second end portion of the at least one channel member, wherein the liquefied sample is subsequently partitioned into said discrete reaction compartment and at least a portion of the liquefied sample is caused to remain in the reaction compartment; and wherein excess liquefied sample is caused to be deposited in the overflow well; and analyzing microbial concentrations in the liquefied sample.

10. The method according to claim 9, wherein the liquefied sample is mixed with microbiological media prior to introducing the liquefied sample to the device.

11. The method according to claim 9, wherein the device has microbiological media associated therewith in a manner that allows mixing with the liquefied sample upon the step of introducing the liquefied sample to the device.

12. The method according to claim 9, further comprising the step of treating the at least one channel member in a manner to enhance capillary flow of a liquid.

13. The method according to claim 9, wherein the step of introducing a quantity of the liquid sample includes introducing approximately 1 ml to approximately 5 ml of liquid sample to the sample receiving well.

14. The method according to claim 9, further including the steps of:

counting positive targets; and comparing the positive targets to an MPN table.

15. The method according to claim 9, wherein the device further includes a cap configured to sealingly close an opening formed in the top member, wherein the method further includes:

introducing the liquid sample to the sample receiving well through the opening in the top member; and placing the cap on the top member to close the opening.

16. The method according to claim 15, wherein the device includes an absorbent material disposed in the cap, and wherein the method further includes the step of inverting the device after the cap has been placed on the lid.

17. The method according to claim 1, further comprising the step of treating the at least one channel member in a manner to enhance capillary flow of a liquid.

18. The method according to claim 1, wherein the step of introducing a quantity of the liquid sample includes introducing approximately 1 ml to approximately 5 ml of liquid sample to the sample receiving well.

19. The method according to claim 1, further comprising the steps of:

incubating the testing device at a predetermined temperature for a predetermined amount of time for a particular test;

counting positive targets; and comparing the positive targets to an MPN table.

20. The method according to claim 1, wherein the device further includes a cap configured to sealingly close an opening formed in the top member, wherein the method further includes:

introducing the liquid sample to the sample receiving well through the opening in the top member; and placing the cap on the top member to close the opening.

21. The method according to claim 20, wherein the device includes an absorbent material disposed in the cap, and wherein the method further includes the step of inverting the device after the cap has been placed on the lid.

22. The method according to claim 4, wherein the liquefied sample is mixed with microbiological media prior to introducing the liquefied sample to the liquid sample testing device.

23. The method according to claim 4, wherein the liquid sample testing device has microbiological media associated therewith in a manner that allows mixing with the liquefied sample upon the step of introducing the liquefied sample to the liquid sample testing device.

24. The method according to claim 4, further comprising the step of treating the at least one channel member in a manner to enhance capillary flow of a liquid.

* * * * *